United States Patent
Brahmbhatt et al.

(10) Patent No.: US 10,098,847 B2
(45) Date of Patent: *Oct. 16, 2018

(54) BACTERIALLY-DERIVED, INTACT MINICELLS THAT ENCOMPASS PLASMID-FREE FUNCTIONAL NUCLEIC ACID FOR IN VIVO DELIVERY TO MAMMALIAN CELLS

(71) Applicant: EnGeneIC Molecular Delivery Pty Ltd, Sydney (AU)

(72) Inventors: Himanshu Brahmbhatt, Sydney (AU); Jennifer MacDiarmid, Sydney (AU); Toby Hulf, Castle Cary (GB)

(73) Assignee: EnGeneIC Molecular Delivery Pty Ltd, Sydney (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/744,848

(22) Filed: Jun. 19, 2015

(65) Prior Publication Data

US 2016/0051687 A1  Feb. 25, 2016

Related U.S. Application Data

(60) Continuation of application No. 14/207,304, filed on Mar. 12, 2014, now Pat. No. 9,066,982, which is a continuation of application No. 13/912,890, filed on Jun. 7, 2013, now Pat. No. 8,956,864, which is a continuation of application No. 12/980,781, filed on Dec. 29, 2010, now Pat. No. 8,669,101, which is a division of application No. 12/053,197, filed on Mar. 21, 2008, now Pat. No. 8,735,566, and a continuation-in-part of application No. 11/211,098, filed on Aug. 25, 2005, now Pat. No. 8,691,963.

(60) Provisional application No. 60/909,074, filed on Mar. 30, 2007, provisional application No. 60/604,433, filed on Aug. 26, 2004.

(51) Int. Cl.

| | |
|---|---|
| C07H 21/02 | (2006.01) |
| C07H 21/04 | (2006.01) |
| A61K 48/00 | (2006.01) |
| A61K 9/50 | (2006.01) |
| C07K 16/12 | (2006.01) |
| C07K 16/28 | (2006.01) |
| C12N 15/11 | (2006.01) |
| C12N 15/113 | (2010.01) |
| A61K 31/713 | (2006.01) |
| A61K 47/46 | (2006.01) |
| A61K 39/40 | (2006.01) |
| C07K 16/40 | (2006.01) |
| A61K 31/4745 | (2006.01) |
| A61K 39/395 | (2006.01) |
| A61K 47/69 | (2017.01) |
| A61K 47/48 | (2006.01) |

(52) U.S. Cl.
CPC ........ *A61K 9/5068* (2013.01); *A61K 31/4745* (2013.01); *A61K 31/713* (2013.01); *A61K 39/39558* (2013.01); *A61K 39/40* (2013.01); *A61K 47/46* (2013.01); *A61K 47/48776* (2013.01); *A61K 47/6901* (2017.08); *A61K 47/6923* (2017.08); *A61K 48/0008* (2013.01); *C07K 16/1235* (2013.01); *C07K 16/2863* (2013.01); *C07K 16/40* (2013.01); *C12N 15/111* (2013.01); *C12N 15/113* (2013.01); *C12N 15/1135* (2013.01); *C12N 15/1137* (2013.01); *C12N 15/1138* (2013.01); *C07K 2317/31* (2013.01); *C12N 2310/11* (2013.01); *C12N 2310/111* (2013.01); *C12N 2310/14* (2013.01); *C12N 2310/141* (2013.01); *C12N 2310/531* (2013.01); *C12N 2320/32* (2013.01)

(58) Field of Classification Search
CPC ..... A61K 48/00; A61K 31/713; C12N 15/111
See application file for complete search history.

(56) References Cited

U.S. PATENT DOCUMENTS

| | | | |
|---|---|---|---|
| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 4,496,778 | A | 1/1985 | Myers et al. |
| 4,975,278 | A | 12/1990 | Senter et al. |
| 5,260,203 | A | 11/1993 | Ladner et al. |

(Continued)

FOREIGN PATENT DOCUMENTS

| | | |
|---|---|---|
| JP | 10-75793 | 3/1998 |
| JP | 10-502819 | 3/1998 |

(Continued)

OTHER PUBLICATIONS

Bertrand et al. (Biochemical and Biophysical Research Communications, 296, 2002, 1000-1004).*

Aagaard, et al., "RNAi therapeutics: Principles, prospects and challenges." *Advanced Drug Delivery Reviews 59*. 2007. pp. 75-86.

Barr et al., "Polo-Like Kinases and the Orchestration of Cell Division", Nature Reviews/Molecular Cell Biology vol. 5, Jun. 2004, pp. 429-440.

Bates et al., "Dynamics of DNA Molecules in a Membrane Channel Probed by Active Control Techniques." *Biophysical Journal*. 2003. vol. 84. pp. 2366-2372.

(Continued)

*Primary Examiner* — Amy H Bowman
(74) *Attorney, Agent, or Firm* — Foley & Lardner LLP

(57) ABSTRACT

Intact, bacterially-derived minicells can safely introduce therapeutically effective amounts of plasmid-free functional nucleic acid to target mammalian cells. To this end, functional nucleic acid can be packaged into intact minicells directly, without resort to expression constructs, the expression machinery of the host cell, harsh chemicals or electroporation.

39 Claims, 7 Drawing Sheets

Specification includes a Sequence Listing.

(56) References Cited

U.S. PATENT DOCUMENTS

| | | | |
|---|---|---|---|
| 5,455,030 | A | 10/1995 | Ladner et al. |
| 6,635,448 | B2 | 10/2003 | Bucciarelli et al. |
| 7,011,946 | B2 | 3/2006 | Raychaudhuri et al. |
| 7,125,679 | B2 | 10/2006 | Ashkar |
| 7,183,105 | B2 * | 2/2007 | Sabbadini ............... C12N 15/00 424/93.1 |
| 2002/0068709 | A1 | 6/2002 | Orum et al. |
| 2003/0203481 | A1 | 10/2003 | Surber et al. |
| 2004/0180844 | A1 * | 9/2004 | Fesik .................. C12N 15/113 514/44 A |
| 2004/0265994 | A1 | 12/2004 | Brahmbatt et al. |
| 2005/0153914 | A1 | 7/2005 | McSwiggen et al. |
| 2007/0166446 | A1 | 7/2007 | Boursier |
| 2007/0237744 | A1 | 10/2007 | Brahmbhatt et al. |
| 2007/0241067 | A1 | 10/2007 | Brahmbhatt et al. |
| 2007/0298056 | A1 | 12/2007 | Brahmbhatt et al. |
| 2008/0038296 | A1 | 2/2008 | Brahmbhatt et al. |
| 2008/0051469 | A1 | 2/2008 | Brahmbhatt et al. |

FOREIGN PATENT DOCUMENTS

| | | |
|---|---|---|
| WO | WO 1981/01145 | 4/1981 |
| WO | WO 1988/07378 | 10/1988 |
| WO | WO 1996/02556 | 2/1996 |
| WO | WO 2000/63364 A2 | 10/2000 |
| WO | WO 2000/67776 | 11/2000 |
| WO | WO 2002/17852 A2 | 3/2002 |
| WO | WO 2003/033519 | 4/2003 |
| WO | WO 03/072014 A2 | 9/2003 |
| WO | WO 2004/022771 A | 3/2004 |
| WO | WO 2005/056749 A2 | 6/2005 |
| WO | WO 2005/079584 A2 | 9/2005 |
| WO | WO 2006/021894 A | 3/2006 |
| WO | WO 2006/066048 A2 | 6/2006 |

OTHER PUBLICATIONS

Batra et al., "Receptor-mediated gene delivery employing lectin-binding specificity", Gene Therapy (1994) 1, 255-260.

Becker et al., "Gene Therapy of Prostate Cancer with the Soluble Vascular Endothelial Growth Factor Receptor Flk1", Cancer Biology & Therapy 1:5, 548-553, Sep./Oct. 2002.

Bertrand et al., "Comparison of antisense oligonucleotides and siRNAs in cell culture and in vivo", Biochemical and Biophysical Research Communications 296 (2002) 1000-1004.

Blangy et al., "Phosphorylation by p34$^{cdc2}$ Regulates Spindle Association of Human Eg5, a Kinesin-Related Motor Essential for Bipolar Spindle Formation in Vivo.", Cell, vol. 83, pp. 1159-1169, Dec. 29, 1995.

Borst et al., "Mammalian ABC Transporters in Health and Disease", Annu. Rev. Biochem. 2002, 71:537-592.

Bredel, "Anticancer drug resistance in primary human brain tumors", Brain Research Reviews, 35 (2001) 161-204.

Bridge et al., "Induction of an interferon response by RNAi vectors in mammalian cells," Nature Genetics, vol. 34, No. 3, (2003), pp. 263-264.

Britton et al., "Characterization of a prokaryotic SMC protein involved in chromosome partitioning", Genes & Development 12:1254-1259, 1998.

Brummelkamp et al., "Stable suppression of tumorigenicity by virus-mediated RNA interference", Cancer Cell, Sep. 2002, vol. 2002, pp. 243-247.

Canadian Office Action Application No. 2 577 938 dated Jul. 28, 2010.

Canadian Office Action Application No. 2 682 704 dated Jun. 6, 2012.

Caplen, "RNAi as a gene therapy approach", Gene Therapy, 2003, pp. 575-586.

Carbone et al., "Multistep and multifactorial carcinogenesis: when does a contributing factor become a carcinogen?," Seminars in Cancer Biology, vol. 14, (2004) pp. 399-405.

Carter, "Improving the Efficacy of Antibody-Based Cancer Therapies", Nature, Nov. 2001, vol. 1, pp. 118-129.

Check, "Gene therapy put on hold as third child develops cancer", Nature, vol. 433, Feb. 10, 2005, p. 561.

Chen et al., "Reversal of Drug Resistance Mediated by Multidrug Resistance Protein (MRP) 1 by Dual Effects of Agosterol A on MRP1 Function", Int. J. Cancer: 93, 107-113 (2001).

Chiu et al., "siRNA function in RNAi: A chemical modification analysis", RNA (2003) 9:1034-1048.

Choung et al., "Chemical modification of siRNAs to improve serum stability without loss of efficacy", Biochemical and Biophysical Research Communications 342 (2006), 919-927.

Colwell et al., "Monoclonal Antibodies to *Salmonella* Lipopolysaccharide: Anti-O-Polysaccharide Antibodies Protect C3H Mice Against Challenge with Virulent *Salmonella typhimurium*," The Journal of Immunology, vol. 133, No. 2, Aug. 1984, pp. 950-957.

Communication pursuant to Article 94(3) EPC EP Application No. 05 806 875.0 dated Dec. 30, 2010.

Conner et al., "Regulated portals of entry into the cell", Nature, vol. 422, Mar. 6, 2003, pp. 37-44.

Czauderna et al., "Structural variations and stabilizing modifications of synthetic siRNAs in mammalian cells", Nucleic Acids Research vol. 31, No. 11, 2003, pp. 2705-2716.

Dagenbach et al., "Erratum—A new kinesin tree", J. Cell Sci. 117, 3-7.

Dash et al., "Factors affecting blood clearance and in vivo distribution of polyelectrolyte complexes for gene delivery", Gene Therapy (1999)6, pp. 643-650.

De Palma et al., "In Vivo Targeting of Tumor Endothelial Cells by Systemic Delivery of Lentiviral Vectors," Human Gene Therapy, vol. 14, Aug. 10, 2003, pp. 1193-1206.

Deboer et al., "Roles of MinC and MinD in the Site-Specific Septation Block Mediated by the MinCDE System of *Escherichia colo*", Journal of Bacteriology, Jan. 1992, vol. 174, No. 1, pp. 63-70.

Decad & Nikaido (1976) "Outer Membrane of Gram-Negative Bacteria: XII. Molecular-Sieving Function of Cell Wall" *Journal of Bacteriology* 128(1):325-336.

Dehaard et al., "A Large Non-immunized Human Fab Fragment Phage Library That Permits Rapid Isolation and Kinetic Analysis of High Affinity Antibodies", The Journal of Biological Chemistry vol. 274, No. 26, Issue of Jun. 25, pp. 18219-18230, 1999.

Delcour, Anne H., "Outer membrane permeability and antibiotic resistance." *Biochemica et Biophysica Acta* 1794. 2009. pp. 806-816.

Devroe et al., "Therapeutic potential of retroviral RNAi vectors", Expert Opin. Biol. Ther. (2004) 4(3):319-327.

Doige et al., "ATP-Dependent Transport Systems in Bacteria and Humans: Relevance to Cystic Fibrosis and Multidrug Resistance", Annu. Rev. Microbiol. 1993, 47:290-319.

Dubel et al., "Bifunctional and multimeric complexes of streptavidin fused to single chain antibodies (scFv)", Journal of Immunological Methods 178 (1995) 201-209.

Dykxhoorn et al., "The Silent Revolution: RNA Interference as Basic Biology, Research Tool and Therapeutic", Annu. Rev. Med. 2005, 56:401-423.

Dykxhoorn et al., "The silent treatment: siRNAs as small molecule drugs", Gene Therapy (2006) 13, 541-552.

Eck et al., "Gene-Based Therapy," Chapter 5, Goodman & Gilman's The Pharmacological Basis of Therapeutics, (1996), pp. 77-102.

Elmen et al., "Locked nucleic acid (LNA) mediated improvements in siRNA stability and functionality", Nucleic Acids Research 2005, vol. 33, No. 1, 439-447.

European search report from corresponding EP application No. 11171410, dated May 30, 2012.

Final Office Action in U.S. Appl. No. 10/602,021 dated May 15, 2007.

Final Office Action in U.S. Appl. No. 11/211,098 dated Feb. 24, 2009.

Final Office Action in U.S. Appl. No. 11/691,698 dated Dec. 29, 2009.

Final Office Action in U.S. Appl. No. 10/581,990 dated Apr. 25, 2012.

Final Office Action in U.S. Appl. No. 10/581,990 dated Jun. 2, 2010.

(56) References Cited

OTHER PUBLICATIONS

Geller et al., "Antisense Phosphorodiamidate Morpholino Oligomer Inhibits Viability of *Escherichia coli* in Pure Culture and in Mouse Peritonitis", Journal of Antimicrobial Chemotherapy, Oxford University Press, GB, vol. 55, May 4, 2005, pp. 983-988, XP003008448.
Glennie et al., "Preparation and Performance of Bispecific F(ab'y)2 Antibody Containing Thioether-Linked Fab'y Fragments", The Journal of Immunology, vol. 139, 2367-2375, No. 7, Oct. 1, 1987.
Glover et al., "Polo-like kinases: a team that plays throughout mitosis", Genes & Development 12:3775-3787.
Gosselin et al., "Folate receptor-targeted liposomes as vectors for therapeutic agents", Biotechnology Annual Review, vol. 8, pp. 103-131, 2002.
Gottesman et al., "Multidrug Resistance in Cancer: Role of ATP-Dependent Transporters", Nature Reviews/Cancer vol. 2, Jan. 2002, pp. 48-58.
Griffiths et al., "Isolation of high affinity human antibodies directly from large synthetic repertoires", The EMBO Journal, vol. 13, No. 14, pp. 3245-3260, 1994.
Grillot-Courvalin et al., "Wild-type intracellular bacteria delivery DNA into mammalian cells," Cellular Microbiology, vol. 4, No. 3, (2002), pp. 177-186.
Grishok et al., "Genetic Requirements for Inheritance of RNAi in C. elegans", Science, vol. 287, Mar. 31, 2000, pp. 2494-2497.
Guerrier-Takada et al., "The RNA Moiety of Ribonuclease P is the Catalytic Subunit of the Enzyme", Cell, vol. 35, 849-857, Dec. 1983 (Part 2).
Hacein-Bey-Abina et al., "LMO2-Associated Clonal T Cell Proliferation in Two Patients after Gene Therapy for SCID-XI", Science, vol. 302, Oct. 17, 2003, pp. 415-419.
Hampel et al., "'Hairpin' catalytic RNA model: evidence for helices and sequence requirement for substrate RNA", Nucleic Acids Research vol. 18, No. 2, pp. 299-304.
Hampel et al., "RNA Catalytic Properties of the Minimum (−)Strsv Sequence", Biochemistry 1989, 28, 4929-4933.
Hanada et al., "Structure-Function Analysis of Bcl-2 Protein", The Journal of Biological Chemistry, vol. 270, No. 20, Issue of May 19, 1995, pp. 11962-11969.
Harry, "Bacterial cell division: regulating Z-ring formation", Molecular Microbiology (2001) 40(4) 795-803.
Harth et al., "Treatment of *Mycobacterium tuberculosis* with antisense oligonucleotides to glutamine synthetase mRNA inhibits glutamine synthetase activity, formation of the poly-L-glutamate/glutamine cell wall structure, and bacterial replication", Proceedings of the National Academy of Sciences of the United States of America, Jan. 2000, vol. 97, No. 1, pp. 418-423, XP002518881.
Higgins, "ABC transporters: physiology, structure and mechanism—an overview", Res. Microbiol. 152 (2001) 205-210.
Hiraga et al., "Chromosome Partitioning in *Eschericia coli*: Novel Mutants Producing Anuleate Cells", Journal of Bacteriology, Mar. 1989, pp. 1496-1505.
Hong et al., "Antisense Bcl2 oligonucleotide in cisplatin-resistant bladder cancer cell lines," BJU International, vol. 90, (2002), pp. 113-117.
Hosida et al., "Gene Therapy for Pancreatic Cancer Using an Adenovirus Vector Encoding Soluble flt-1 Vascular Endothelial Growth Factor Receptor", Pancreas, vol. 25, No. 2, pp. 111-121.
Hu et al., "Topological regulation of cell division in *Escherichia coli* involves rapid pole to pole oscillation of the division inhibitor MinC under the control of MinD and MinE", Molecular Microbiology (1999) 34(1), 82-90.
Hung et al., "16—Development of Clinical Trial of E1A Gene Therapy Targeting HER-2lneu-Overexpressing Breast and Ovarian Cancer", Cancer Gene Therapy: Past Achievements and Future Challenges, 2000, pp. 171-180.
International Search Report PCT/IB2008/002984 dated Mar. 26, 2009.
Ireton et al., "spo0J Is Required for Normal Chromosome Segregation as well as the Initiation of Sporulation in *Bacillus subtilis*"Journal of Bacteriology, vol. 176, No. 17, Sep. 1994, pp. 5320-5329.

Jennifer A. MacDiarmid et al., "Bacterially derived 400 nm particles for encapsulation and cancer cell targeting of chemotherapeutics", Cancer Cell, vol. 11, No. 5, May 1, 2007, pp. 431-445.
Jones et al., "Replacing the complementarity-determining regions in a human antibody wit those from a mouse", Nature, vol. 321, May 29, 1986, pp. 522-525.
Kaetzel et al., "The polymeric immunoglobulin receptor: structure and synthesis", Biochemical and Society Transactions, Immunoglobulins and Mechanisms of Mucosal Immunity, vol. 25, 1997, pp. 475-480.
Kapoor et al., "Probing Spindle Assembly Mechanisms with Monastrol, a Small Molecule Inhibitor of the Mitotic Kinesin, Eg5", The Journal of Cell Biology, vol. 150, No. 5, Sep. 4, 2000, pp. 975-988.
Karagiannis & Anderson (2009) "Minicells overcome tumor drug-resistance" *Nature Biotechnology* 27(7):620-621.
Karpovsky et al., "Production of Target-Specific Effector Cells Using Hetero-Cross-Linked Aggregates Containing Anti-Target Cell and Anti-Fcγ Receptor Antibodies", Journal of Experimental Medicine, vol. 160, Dec. 1984, pp. 1686-1701.
Kelland, "Of mice and men": values and liabilities of the athymic nude mouse model in anticancer drug development, European Journal of Cancer, vol. 40, (2004), pp. 827-836.
Kerbel, "What is the optimal rodent model for anti-tumor drug testing?," Cancer and Metastasis Reviews, vol. 17, (1999), pp. 301-304.
Kleeff et al., "Targeting of suicide gene delivery in pancreatic cancer cells via FGF receptor", Cancer Gene Therapy (2002) 9, pp. 522-532.
Knappik et al., "Fully Synthetic Human Combinatorial Antibody Libraries (HuCAL) Based on Modular Consensus Frameworks and CDRs Randomized with Trinucleotides", J. Mol. Biol. (2000) 296, pp. 57-86.
Kootstra et al., "Gene Therapy with Viral Vectors", Annu. Rev. Pharmacol. Toxicol. 2003, 43:413-439.
Kostelny et al., "Formation of a B Specific Antibody by the Use of Leucine Zippers", The Journal of Immunology, vol. 148, No. 5, Mar. 1, 1992, pp. 1547-1553.
Kruh et al., "The MRP family of drug efflux pumps", Oncogene (2003) 22, pp. 7537-7552.
Kunz-Schughart et al., "The Use of 3-D Cultures for High-Throughput Screening: The Multicellular Spheriod Model," Journal of Biomolecular Screening, vol. 9, (2004), pp. 273-285.
Layzer et al., "In vivo activity of nuclease-resistant siRNAs", RNA (2004) 10:766-771.
Lee et al., "The C. elegans Heterochronic Gene lin-4 Encodes Small RNAs with Antisense Complementarity to lin-14", Cell, vol. 75, Dec. 3, 1993, pp. 843-854.
Leng et al. (2009) "Advances in Systemic siRNA Delivery" *Drugs Future* 34(9):721.
Lu et al., "Delivery of adenoviral vectors to the prostate for gene therapy," Cancer Gene Therapy, vol. 6, No. 1, (1999), pp. 64-72.
MacDiarmid et al. (2009) "Sequential treatment of drug-resistant tumors with targeted minicells containing siRNA or a cytotoxic drug" *Nature Biotechnology* 27(7):643-651.
MacDiarmid et al., "Reversal of drug resistance in cancer: Target delivery of siRNA and drugs in vivo via biologically derived nanoparticles", Proceedings of the American Association for Cancer Research Annual Meeting, vol. 48, Apr. 2007, p. 1371, XP001537093 & 98th Annual Meeting for the American-Association-For-Cancer-Research; Los Angeles, CA, USA; Apr. 14-18, 2007.
Marshall, "Carcinoembryonic Antigen-Based Vaccines", Seminars in Oncology, vol. 30, No. 3, Supp. 8, Jun. 2003, pp. 30-36.
Mayer et al., "Small Molecule Inhibitor of Mitotic Spindle Bipolarity Identified in a Phenotype-Based Screen", Science, vol. 286, Oct. 29, 1999, pp. 971-974.
McCluskie et al., "Route and Method of Delivery of DNA Vaccine Influence Immune Responses in Mice and Non-Human Primates," Molecular Medicine, vol. 5, (1999), pp. 287-300.
McManus et al., "Gene Silencing in Mammals by Small Interfering RNAs", Nature Reviews, Genetics, vol. 3, Oct. 2002, pp. 737-747.
McNamara et al. (2006) "Cell type-specific delivery of siRNAs with aptamer-siRNA chimeras" *Nature Biotechnology* 24(8):1005-1015.

(56) References Cited

OTHER PUBLICATIONS

Miller, "[30] Bacterial Transformation by Electroporation", Bacterial Electroporation, Methods in Enzymology, vol. 235, 1994, pp. 375-385.

Modok et al., "Modulation of multidrug resistance efflux pump activity to overcome chemoresistance in cancer", Current Opinion in Pharmacology 2006, 6:350-354.

Monia et al., "Nuclease Resistance and Antisense Activity of Modified Oligonucleotides Targeted to Ha-ras", The Journal of Biological Chemistry, vol. 271, No. 24, Issue of Jun. 14, 1996, pp. 14533-14540.

Morrissey et al., "Activity of Stabilized Sort Interfering RNA in a Mouse Model of Hepatitis B Virus Replication", Hepatology 2005; 41:1349-1356.

Notice of Reasons for Rejection Japanese Patent Application No. 2007-529046 dated Jun. 28, 2011.

Nicholson et al., "EGFR and cancer prognosis", European Journal of Cancer 37 (2001) S9-S15.

Nikaido, "Prevention of Drug Access to Bacterial Targets: Permeability Barriers and Active Efflux", Science, vol. 264, Apr. 15, 1994, pp. 382-388.

Nikaido, Hiroshi, "Prevention of drug access to bacterial targets: permeability barriers and active efflux." Science. 1994. Volume 264. pp. 382-388.

Non-Final Office Action in U.S. Appl. No. 11/211,098 dated Apr. 24, 2008.

lNon-Final Office Action in U.S. Appl. No. 11/211,098 dated Aug. 7, 2009.

Non-Final Office Action in U.S. Appl. No. 11/691,698 dated Dec. 24, 2008.

Non-Final Office Action in U.S. Appl. No. 10/581,990 dated Mar. 19, 2009.

Non-Final Office Action in U.S. Appl. No. 10/581,990 dated Feb. 26, 2014.

Non-Final Office Action in U.S. Appl. No. 10/581,990 dated Sep. 22, 2011.

Non-Final Office Action in U.S. Appl. No. 10/588,028 dated Mar. 18, 2009.

Non-Final Office Action in U.S. Appl. No. 10/602,021 dated May 4, 2006.

Non-Final Office Action in U.S. Appl. No. 10/602,021 dated Jul. 25, 2008.

Non-Final Office Action in U.S. Appl. No. 11/211,098 dated Sep. 23, 2010.

Non-Final Office Action in U.S. Appl. No. 11/765,635 dated Oct. 6, 2009.

Non-Final Office Action in U.S. Appl. No. 11/765,635 dated Mar. 29, 2010.

Non-Final Office Action in U.S. Appl. No. 12/053,197 dated Aug. 25, 2009.

Non-Final Office Action in U.S. Appl. No. 12/053,197 dated Mar. 10, 2010.

Notice of Allowance in U.S. Appl. No. 10/602,021 dated Jun. 22, 2009.

Notice of Allowance in U.S. Appl. No. 11/691,698 dated Jan. 4, 2011.

Notice of Allowance in U.S. Appl. No. 11/691,698 dated Sep. 2, 2010.

Notice of Allowance in U.S. Appl. No. 12/053,197 dated Jan. 16, 2014.

Okada et al., "Cytoplasmic Axial Filaments in *Escherichia coli* Cells: Possible Function in the Mechanism of Chromosome Segregation and Cell Division", Journal of Bacteriology, vol. 176, No. 3, Feb. 1994, pp. 917-922.

Opalinska et al., "Nucleic-Acid Therapeutics: Basic Principles and Recent Applications", Nature Reviews, Drug Discover, vol. 1, Jul. 2002, pp. 503-514.

Osbourn et al., "Current methods for the generation of human antibodies for the treatment of autoimmune diseases", Drug Discovery Today, vol. 8, No. 18, Sep. 2003, pp. 845-851.

Pack et al., "Miniantibodies: Use of Amphipathic Helices to Produce Functional, Flexibly Linked Dimeric Fv Fragments with High Avidity in *Escherichia coli*", Biochemistry, vol. 31, No. 6, Feb. 18, 1992, pp. 1579-1584.

Paddison et al., "Short hairpin RNAs (shRNAs) induce sequence-specific silencing in mammalian cells", Genes and Development 16:948-958, 2002.

Palione et al., "Mutation of a Gene That Encodes a Kinesin-like Protein Blocks Nuclear Division in A. nidulans", Cell, vol. 60, 1019-1027, Mar. 23, 1990.

Panja et al., "How does plasmid DNA penetrate cell membranes in artificial transformation process of *Escherichia coli*." Molecular Membrane Biology. 2008. vol. 25 No. 5. pp. 411-422.

Perrotta et al., "Cleavage of Oligoribonucleotides by a Ribozyme Derived from the Hepatitis $\delta$ Virus RNA Sequence", Biochemistry 1992, 31, pp. 16-21.

Pikaar et al., "Opsonic Activities of Surfactant Proteins A and D in Phagocytosis of Gram-Negative Bacteria by Alveolar Macrophages", The Journal of Infectious Diseases, 1995, 172:481-489.

Raper et al., "Fatal systemic inflammatory response syndrome in a ornithine transcarbamylase deficient patient following adenoviral gene transfer", Molecular Genetics and Metabolism 80 (2003) 148-158.

Raskin et al., "MinDE-Dependent Pole-to-Pole Oscillation of Division Inhibitor MinC in *Escherichia coli*", Journal of Bacteriology, vol. 181, No. 20, Oct. 1999, pp. 6419-6424.

Reeve et al., "Bacteriophage SPO1-Induced Macromolecular Synthesis in Minicells of *Bacillus subtilis*", Journal of Virology, vol. 15, No. 5, Jun. 1975, pp. 1308-1316.

Ridgway et al., "Knobs-into-holes engineering of antibody CH3 domains for heavy chain heterodimerization", Protein Engineering vol. 9, No. 7, pp. 617-621, 1996.

Riechmann et al., "Reshaping human antibodies for therapy", Nature, vol. 332, Mar. 24, 1988, pp. 323-327.

Riezman, "Three clathrin-dependent budding steps and cell polarity", Trends in Cell Biology, vol. 3, Oct. 1993, pp. 330-332.

Rossi et al., "Ribozymes as Anti-HIV-1 Therapeutic Agents: Principles Applications and Problems", AIDS Research and Human Retroviruses, vol. 8, No. 2, 1992, pp. 183-189.

Salomon et al., "Epidermal growth factor-related peptides and their receptors in human malignancies", Critical Reviews in Oncology/Hematogology, 19 (1995) pp. 183-232.

Sandvig et al., "Endocytosis without clathrin", Trends in Cell Biology, vol. 4, Aug. 1994, pp. 275-277.

Sawin et al., "Mutations in the kinesin-like protein Eg5 disrupting localization to the mitotic spindle", Cell Biology, Proc. Natl. Acad. Sci. USA, vol. 92, pp. 4289-4293, May 1995.

Sellers et al., "Apoptosis and cancer drug targeting", The Journal of Clinical Investigation, Dec. 1999, vol. 104, No. 12, pp. 1655-1661.

Seville et al., "A Site-Specific Self-Cleavage Reaction Performed by a Novel RNA in Neurospora Mitochondria", Cell, vol. 61, May 18, 1990, pp. 685-696.

Seville et al., "RNA-mediated ligation of self-cleavage products of a *Neurospora* mitochondrial plasmid transcript", Proc. Natl. Acad. Sci. USA, vol. 88, pp. 8826-8830, Oct. 1991.

Sheets et al., "Efficient construction of a large nonimmune phage antibody library: The production of high-affinity human single-chain antibodies to protein antigens", Proc. Natl. Acad. Sci. USA, vol. 95, pp. 6157-6162, May 1998.

Shen, et al., "Reversal of multidrug resistance of gastric cancer cells by downregulation of TSG101 with TSG101siRNA", Cancer Biology & Therapy, vol. 3, No. 6, pp. 561-565, (2004).

Singh, "Transferring As a Targeting Ligand for Liposomes and Anticancer Drugs", Current Pharmaceutical Design 1999, 5, 443-451.

Sioud, "Therapeutic siRNAs", Trends in Pharacological Sciences, vol. 25, No. 1, Jan. 2004, pp. 22-28.

Souriau et al., "Recombinant antibodies for cancer diagnosis and therapy", Expert Opin. Biol. Ther. (2001) 1(5), pp. 845-855.

Speert et al., "Functional Characterization of Macrophage Receptors for In Vitro Phagocytosis of Unopsonized *Pseudomonas aeruginosa*", J. Clin. Invest. vol. 82, Sep. 1988, pp. 872-879.

(56) References Cited

OTHER PUBLICATIONS

Stewart et al., "Genetic and Morphological Characterization of an *Escherichia coli* Chromosome Segregation Mutant", Journal of Bacteriology, vol. 174, No. 13, Jul. 1992, pp. 4513-4516.
Stockert, "The Asialoglycoprotein Receptor: Relationships Between Structure Function and Expression", Physiological Reviews, vol. 75, No. 3, Jul. 1995, pp. 591-609.
Strebhardt et al., "Targeting polo-like kinase 1 for cancer therapy", Nature Reviews, Cancer, vol. 6, Apr. 2006, pp. 321-330.
Sun et al., "Overexpression of Bcl2 Blocks TNF-Related Apoptosis-Inducing Ligand (TRAIL)-Induced Apoptosis in Human Lung Cancer Cells", Biochemical and Biophysical Research Communications 280, 788-797 (2001).
Supplementary European Search Report EP 05 80 6875 dated Jan. 26, 2009.
Tao et al., "Induction of apoptosis by an inhibitor of the mitotic kinesin KSP requires both activation of the spindle assembly checkpoint and mitotic slippage", Cancer Cell, Jul. 2005, vol. 8, pp. 49-59.
Thurnher et al., "Carbohydrate receptor-mediated gene transfer to human T leukaemic cells", Glycobiology, vol. 4, No. 4, pp. 429-435, 1994.
Todorovska et al., "Design and application of diabodies, triabodies and tetrabodies for cancer targeting", Journal of Immunological Methods, 248 (2001) 47-66.
Tomlinson et al., "[28] Methods for Generating Multivalent and Bispecific Antibody Fragments", Multivalent and Bispecific Antibody Fragments, Methods in Enzymology, vol. 326, pp. 461-479, 2000.
Van De Weerdt et al., "Polo-Like Kinases A Team in Control of the Division", Cell Cycle 5:8, 853-864, Apr. 15, 2006.
Vaughan et al., "Human antibodies by design", Nature Biotechnology, vol. 16, Jun. 1998, pp. 535-539.
Verhoeyen et al., "Reshaping Human Antibodies: Grafting an Antilysozyme Activity", Science, vol. 239, pp. 1534-1536, Mar. 25, 1988.
Verma et al., "Gene Therapy: Twenty-First Century Medicine", Annu. Rev. Biochem. 2005, 74:711-738.
Vickers et al., "Efficient Reduction of Target RNAs by Small Interfering RNA and RNase H-dependent Antisense Agents", The Journal of Biological Chemistry, vol. 278, No. 9, Issue of Feb. 2, 2003, pp. 7108-7118.
Wachi et al., "New mre Genes mreC and mreD, Responsible for Formation of the Rod Shape of *Escherichia coli* Cells", Journal of Bacteriology, vol. 171, No. 12, Dec. 1989, pp. 6511-6516.
Wang et al., "Control of inducible chemoresistance: Enhanced anti-tumor therapy through increased apoptosis by inhibition of NF-κB", Nature Medicine, vol. 5, No. 4, Apr. 1999, pp. 412-417.
White et al., "Suppression of apoptosis: role in cell growth and neoplasia", Leukemia (2001) 15, 1011-1021.
Whitehead et al., "Knocking down barriers: advances in siRNA delivery." Nature Reviews Drug Discovery 8. 2009. pp. 129-138.
Wright et al., "Interferon-γ Depresses Binding of Ligand by C3b and C3bi Receptors on Cultured Human Monocytes an Effect Reversed by Fibronectin," J. Exp. Med. vol. 163, May 1986, 1245-1259.
Wu et al., "Small Interfering RNA-induced Suppression of MDRI (P-Glycoprotein) Restores Sensitivity to Multidrug-resistant Cancer Cells," Cancer Research, vol. 63, Apr. 1, 2003, pp. 1515-1519.
Wu et al., "Small Interfering RNA-induced Suppression of MDR1 (P-Glycoprotein) Restores Sensitivity to Multidrug-resistant Cancer Cells", Cancer Research 63, 1515-1519, Apr. 1, 2003.
Xu, et al., "Strategies for inhibition of MDR1 gene expression", Molecular Pharmacology, vol. 66, No. 2, pp. 268-275, (2004).
Yague et al., "Complete reversal of multidrug resistance by stable expression of small interfering RNAs 1 targeting MDR1", Gene Therapy, (2004) 11, 1170-1174.
Yanagihara et al., "Effects of short interfering RNA against methicillin-resistant *Staphylococcus aureus* coagulase in vitro and in vivo", The Journal of Antimicrobial Chemotherapy, Jan. 2006, vol. 57, No. 1, Jan. 2006, pp. 122-126, XP002518418.
Yanagihara et al., "Effects of short interfering RNA against methicillin-resistant *Staphylococcus aureus* coagulase in vitro and in vivo." Journal of Antimicrobial Chemotherapy. 2006. volume 57. pp. 122-126.
Zamore et al., "RNAi: Double-Stranded RNA Directs the ATP-Dependent Cleavage of mRNA at 21 to 23 Nucleotide Intervals", Cell., vol. 101, 25-33, Mar. 31, 2000.
Zamore, "Ancient Pathways Programmed by Small RNAs", Science, vol. 296, May 17, 2002, pp. 1265-1269.
Ziady et al., "Gene transfer into hepatoma cell lines via the serpin enzyme complex receptor", Am. J. Physiol. 273: G545-G552 (1997).
Office Action issued in related U.S. Appl. No. 13/912,890, dated Aug. 19, 2014.
Office Action issued in related U.S. Appl. No. 13/912,890, dated Mar. 20, 2014.
U.S. Office Action issued in related U.S. Appl. No. 14/152,979, dated Jun. 9, 2015.
Office Action issued in related U.S. Appl. No. 14/983,126, dated May 26, 2016.
Notice of Allowance issued in related U.S. Appl. No. 14/983,126, dated Apr. 12, 2017.
Supplemental Notice of Allowance issued in related U.S. Appl. No. 14/983,126, dated Apr. 26, 2017.
Office Action issued in related U.S. Appl. No. 14/983,126, dated Jan. 31, 2017.
Search Report and Written Opinion issued in related Singapore Patent Application No. 10201507969P, dated Mar. 27, 2017.
Giacalone, et al., Immunization with non-replicating *E. coli* minicells delivering both protein antigen and DNA protects mice from lethal challenge with lymphocytic choriomeningitis virus, Vaccine, vol. 25, No. 12, pp. 2279-2287 (2006).

* cited by examiner

1μ m

1μ m

SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
ggtggatgtg tggtccattt t                                         21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
aactggatcg taagaaggca g                                         21

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
ctgaagacct gaagacaat                                            19

BACTERIALLY-DERIVED, INTACT MINICELLS THAT ENCOMPASS PLASMID-FREE FUNCTIONAL NUCLEIC ACID FOR IN VIVO DELIVERY TO MAMMALIAN CELLS

CROSS-REFERENCE TO RELATED PATENT APPLICATIONS

This application is a continuation of U.S. patent application Ser. No. 14/207,304, filed Mar. 12, 2014, which is a continuation of U.S. patent application Ser. No. 13/912,890, filed Jun. 7, 2013, now U.S. Pat. No. 8,956,864, which is a continuation of Ser. No. 12/980,781, filed Dec. 29, 2010, now U.S. Pat. No. 8,669,101, which is a divisional of U.S. patent application Ser. No. 12/053,197, filed Mar. 21, 2008, now U.S. Pat. No. 8,735,566, which claims the benefit of priority from U.S. Provisional Patent Application No. 60/909,074, filed Mar. 30, 2007, and is a continuation-in-part of U.S. patent application Ser. No. 11/211,098, filed Aug. 25, 2005, now U.S. Pat. No. 8,691,963, which claims the benefit of priority from U.S. Provisional Patent Application No. 60/604,433, filed Aug. 26, 2004. The contents of each of these applications are incorporated herein by reference in their entirety.

BACKGROUND OF THE INVENTION

Recently, a number of nucleic acid-based strategies have been developed to modulate a variety of cellular functions (Opalinska and Gewirtz, 2002). Classes of oligonucleotides such as aptamers, transcription factor-binding decoy oligonucleotides, ribozymes, triplex-forming oligonucleotides, immunostimulatory CpG motifs, antisense oligonucleotides (including peptide nucleic acids), small interfering RNAs, and microRNAs have drawn much interest as research tools, owing to their highly specific mode of action. These oligomeric nucleic acids have considerable potential as therapeutics, too. Such therapeutics face several obstacles, however, including the instability of free nucleic acids and the safe, efficient and targeted cellular delivery of these macromolecules (Dykxhoorn and Lieberman, 2005).

A focus of many nucleic acid-based therapeutic strategies is the phenomenon of RNA interference (RNAi), whereby long, double-stranded RNA (dsRNA) in a cell leads to sequence-specific degradation of homologous (complementary or partially complementary) gene transcripts. More particularly, the long dsRNA molecules are processed into smaller RNAs by an endogenous ribonuclease called "Dicer" (Grishok et al., 2000; Zamore et al., 2000). The smaller RNAs are known as "short interfering RNA" (siRNA) when they derive from exogenous sources and as "microRNA" (miRNA) when they are produced from RNA-coding genes in the cell's own genome. These two classes of small (typically, 21- to 23-nucleotide) regulatory RNAs also differ in that miRNAs show only partial complementarity to messenger RNA (mRNA) targets.

The short regulatory RNAs bind to the so-called "RNA-induced silencing complex" (RISC), which has a helicase activity and an endonuclease activity. The helicase activity unwinds the two strands of RNA molecules, allowing the antisense strand to bind to the targeted RNA molecule (Zamore et al., 2000; Zamore, 2002; Vickers et al., 2003). The endonuclease activity hydrolyzes the target RNA at the site where the antisense strand is bound.

In RNAi, therefore, a single-stranded RNA molecule (ssRNA) binds to the target RNA molecule by Watson-Crick base-pairing rules and recruits a ribonuclease that degrades the target RNA. By contrast, antisense suppression of gene expression entails the binding of ssRNA to mRNA, blocking translation without catalyzing the degradation of the mRNA.

As a class, regulatory RNAs have a half-life of less than an hour in human plasma (Layzer et al., 2004) and are rapidly excreted by the kidneys. Consequently, several groups have attempted to prepare regulatory RNAs, including siRNAs, that are nuclease-resistant. Examples of such efforts include chemically modifying the nucleotides (e.g., 2'-F, 2'-OMe, Locked Nucleic Acids; LNA) or the phosphodiester backbone, e.g., phosphorothioate linkages (Chiu and Rana 2003; Choung et al., 2006; Czauderna et al., 2003; Elmén et al., 2005; Layzer et al., 2004; Morrissey et al., 2005). Also, to minimize the time siRNAs or other regulatory RNAs spend in circulation, practitioners have conjugated the RNA molecules to proteins and antibodies to target desired mammalian cells. In further efforts to address the concerns of low stability and rapid renal excretion, practitioners have developed vehicles for delivering regulatory RNAs. Polyplexes (formed by self assembly of nucleic acids with polycations), lipopolyplexes (formed by initial condensation of the nucleic acid with polycations, followed by addition of cationic lipids), liposomes, and synthetic nanoparticles are being explored, too.

These approaches also face numerous obstacles, such as (a) rapid clearance of the carrier proteins from the serum through renal excretion, (b) limited number of regulatory RNA molecules that can be conjugated to each carrier protein, (c) difficulty in intracellular dissociation of intact, regulatory RNAs from the carrier protein, (d) rapid clearance due to polyplexes binding serum proteins which can act as opsonins (Dash et al., 1999), and (e) instability of liposomes in vivo, causing release of nucleic acids into the serum and potential non-specific transformation.

Viral vectors also have been developed to produce regulatory RNAs endogenously. See, e.g., Devroe and Silver, 2004. These viral vectors pose serious safety concerns, however. Illustrative problems include recombination with wild-type viruses, insertional and oncogenic potential, virus-induced immunosuppression, limited capacity of the viral vectors to carry large segments of DNA, reversion to virulence of attenuated viruses, difficulties in manufacture and distribution, low stability, and adverse reactions (Hacein-Bey-Abina et al., 2003; Kootstra and Verma, 2003; Raper et al., 2003; Verma and Weitzman, 2005; Check, 2005).

Plasmid-based systems also have been developed for recombinant, in situ expression of a regulatory RNA, such as an siRNA or a larger (~70 nt) precursor, a short hairpin RNA (shRNA). An shRNA contains sense and antisense sequences from a target gene that are connected by a hairpin loop. See, e.g., Paddison et al., 2002. shRNAs can be expressed from a pol-III-type promoter or, in the context of a miRNA, by pol II promoters.

As described in international application WO 03/033519, plasmids that code for an shRNA, siRNA, or other regulatory RNA can be transformed into a parent bacterial strain that produces intact minicells, by virtue of a mutation that causes asymmetric cell division. Such transformation yields recombinant bacteria in which the plasmid replicates intracellularly, introducing large numbers of plasmids in the bacterial cytoplasm. During the asymmetric division, some of the plasmids segregate into the minicell cytoplasm, resulting in recombinant minicells. The minicells then can deliver the plasmid DNA into a mammalian cell, where the plasmid DNA migrates to the cell nucleus. In the nucleus the plasmid DNA expresses the shRNA or other regulatory RNA, as the case may be, and the resultant nucleic acid then migrates to the cytoplasm, where it can effect RNAi or gene suppression, depending on the nature of the involved regulatory RNA.

Because such approaches require host machinery, however, delivering therapeutically effective amounts of nucleic acid via expression-based systems involves complex and protracted processes, which limits their effectiveness. Accordingly, a more efficacious methodology is needed for delivering functional nucleic acids, such as regulatory RNAs, to target cells.

SUMMARY OF THE INVENTION

In accordance with one aspect of the invention, therefore, a composition comprising (a) a plurality of intact minicells, each minicell of the plurality encompassing plasmid-free functional nucleic acid, and (b) a pharmaceutically acceptable carrier therefor. The category of "functional nucleic acid" is illustrated by single-, double-, or multi-stranded DNA or RNA. In one embodiment, minicells of the plurality contain plasmid-free functional nucleic acid that is regulatory RNA. Examples of such regulatory RNA include, but are not limited to, siRNA, miRNA, and shRNA.

The minicell-packaged functional nucleic acid may target the RNA transcripts encoding a protein that contributes to drug resistance, to apoptosis resistance, or to neoplasticity, inter alia. Also, a composition of the invention may further comprise a bispecific ligand comprised, for example, of a first arm specific for a minicell surface structure and a second arm specific for a non-phagocytic mammalian cell surface receptor.

In another aspect of the invention, a method is provided for delivering a functional nucleic acid to a target mammalian cell. The inventive methodology comprises (a) providing a plurality of intact minicells in a pharmaceutically acceptable carrier, each minicell of the plurality encompassing plasmid-free functional nucleic acid, and (b) bringing minicells of the plurality into contact with mammalian cells such that the mammalian cells engulf minicells of the plurality, whereby the functional nucleic acid is released into the cytoplasm of the target cells. As mentioned, the functional nucleic acid, exemplified by regulatory RNA such as siRNA, miRNA and shRNA, can target RNA transcripts encoding a protein that contributes to drug resistance, apoptosis resistance or neoplasticity. In other embodiments, the methodology of the invention further comprises delivering a drug, distinct from the functional nucleic acid, to the target mammalian cell. The drug can be administered after or concurrently or even before the administration of the minicell composition.

In accordance with another aspect, the present invention contemplates a method for formulating a minicell with a plasmid-free functional nucleic acid. The method comprises co-incubating a plurality of minicells with a functional nucleic acid, such as regulatory RNA like siRNA, miRNA or shRNA, in a buffer. In some embodiments, the co-incubation may involve gentle shaking, while in others the co-incubation is static. In some aspects, the co-incubation lasts about half an hour, while in others it lasts about an hour. In one embodiment, the buffer comprises buffered saline, for example, a 1× phosphate buffer solution. In another embodiment, the co-incubation is conducted at a temperature of about 4° C. to about 37° C., about 20° C. to about 30° C., about 25° C., or about 37° C. The co-incubation can comprise about $10^7$, $10^8$, $10^9$, $10^{10}$, $10^{11}$, $10^{12}$ or $10^{13}$ minicells.

Other objects, features and advantages will become apparent from the following detailed description. The detailed description and specific examples are given for illustration only since various changes and modifications within the spirit and scope of the invention will become apparent to those skilled in the art from this detailed description. Further, the examples demonstrate the principle of the invention and cannot be expected to specifically illustrate the application of this invention to all the examples where it will be obviously useful to those skilled in the prior art.

BRIEF DESCRIPTION OF THE DRAWINGS

FIG. 1A is from a light microscope, while FIG. 1B shows the same slide but viewed under fluorescent light with a 515-560 excitation filter revealing strongly fluorescent siRNA molecules coincident with the minicells.

FIGS. 5A-5D provide FACS analysis of samples harvested 4 hours after transfection, while FIGS. 5E-5H show analysis from samples at 8 hours post-transfection. FIGS. 5A & 5E show results from cells only, while FIGS. 5B & 5F concern cells+empty $^{EGFR}$minicells. FIGS. 5C & 5G show results from cells+$^{EGFR}$minicells$_{siRNA-KSP}$, and FIGS. 5D & 5H concern cells+$^{EGFR}$minicells$_{siRNA-Plk1}$.

FIGS. 6A-6D provide FACS analysis of samples harvested 16 hours after transfection, while FIGS. 6E-6H show analysis from samples at 24 hours post-transfection. FIGS. 6A & 6E show results from cells only, while FIGS. 6B & 6F concern cells+empty $^{EGFR}$minicells. FIGS. 6C & 6G show results from cells+$^{EGFR}$minicells$_{siRNA-KSP}$, and FIGS. 6D & 6H concern cells+$^{EGFR}$minicells$_{siRNA-Plk1}$.

FIGS. 7A-7D provide FACS analysis of samples harvested 32 hours after transfection, while FIGS. 7E-7H show analysis from samples at 48 hours post-transfection. FIGS. 7A & 7E show results from cells only, while FIGS. 7B & 7F concern cells+empty $^{EGFR}$minicells. FIGS. 7C & 7G show results from cells+$^{EGFR}$minicells$_{siRNA-KSP}$, and FIGS. 7D & 7H concern cells $^{EGFR}$minicells$_{siRNA-Plk1}$.

DETAILED DESCRIPTION OF THE INVENTION

Figure 1A:
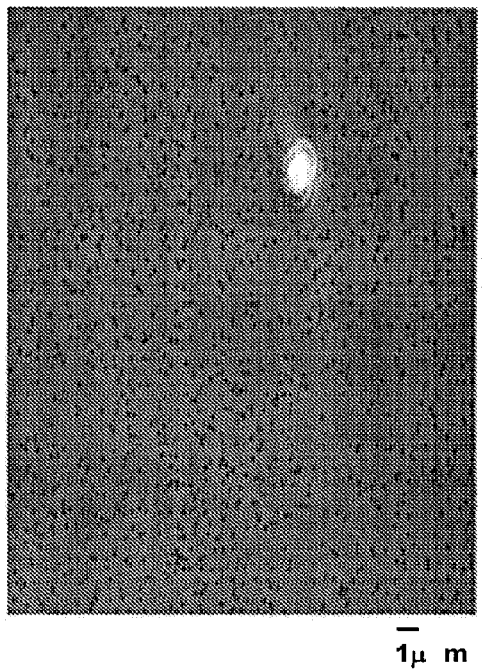
FIGS. 1A-1B depicts intact minicells packaged with Cy3 fluorophore-labeled siRNA.

Pursuant to the present invention, therapeutically effective amounts of functional nucleic acid can be packaged into minicells without resort to harsh chemicals or electroporation. In this regard, a simple methodology for directly packaging such therapeutically effective concentrations of functional nucleic acids into intact minicells has been developed that does not involve plasmid-based expression constructs or the expression machinery of a host bacterial cell. Accordingly, a polynucleotide segment that codes for the functional nucleic acid is not cloned into a plasmid DNA or viral vector. Instead, the plasmid-free functional nucleic acids are packaged directly into the minicells by passing through the minicell's intact membrane. Moreover, a minicell composition of the invention safely and effectively can deliver, to targeted mammalian cells, therapeutically effective amounts of functional nucleic acid molecules, illustrated by regulatory RNAs such as siRNAs, miRNAs, and shRNAs.

Definitions

Unless defined otherwise, all technical and scientific terms used in this description have the same meaning as commonly understood by those skilled in the relevant art.

For convenience, the meaning of certain terms and phrases employed in the specification, examples, and appended claims are provided below. Other terms and phrases are defined throughout the specification.

The singular forms "a," "an," and "the" include plural reference unless the context clearly dictates otherwise.

"Antisense oligonucleotide" refers to a nucleic acid molecule complementary to a portion of a particular gene transcript that can hybridize to the transcript and block its translation. An antisense oligonucleotide can comprise RNA or DNA.

"Biomolecular sequence" or "sequence" refers to all or a portion of a polynucleotide or polypeptide sequence.

"Cancer," "neoplasm," "tumor," "malignancy" and "carcinoma," used interchangeably herein, refer to cells or tissues that exhibit an aberrant growth phenotype characterized by a significant loss of control of cell proliferation. The methods and compositions of this invention particularly apply to malignant, pre-metastatic, metastatic, and non-metastatic cells.

"Complementary" refers to the topological compatibility or matching together of the interacting surfaces of two molecules, such as a siRNA molecule and its target mRNA. The molecules can be described as complementary, and furthermore, the contact surface characteristics are complementary to each other.

"Corresponds to" or "represents" when used in the context of, for example, a polynucleotide or sequence that "corresponds to" or "represents" a gene means that a sequence of the polynucleotide is present in the gene or in the nucleic acid gene product, e.g., mRNA. The polynucleotide can be wholly present within an exon of a genomic sequence of the gene, or different portions of the sequence of the polynucleotide can be present in different exons, e.g., such that the contiguous polynucleotide sequence is present in an mRNA, either pre- or post-splicing, that is an expression product of the gene.

A "decoy RNA" is a molecule which can adopt a structure identical to an important functional region of the RNA to be targeted. The latter RNA can be native to a mammalian host or a pathogen that has infected a mammalian cell, e.g. HIV. The decoy RNA sequesters away the protein that normally interacts with the target RNA resulting in a disruption of normal processing of the mammalian or pathogen host.

"Drug" refers to any physiologically or pharmacologically active substance that produces a local or systemic effect in animals, particularly mammals and humans.

"Expression" generally refers to the process by which a polynucleotide sequence undergoes successful transcription and translation such that detectable levels of the amino acid sequence or protein are expressed. In certain contexts herein, expression refers to the production of mRNA. In other contexts, expression refers to the production of protein.

"Functional nucleic acid" refers to a nucleic acid molecule that, upon introduction into a host cell, specifically interferes with expression of a protein. In general, functional nucleic acid molecules have the capacity to reduce expression of a protein by directly interacting with a transcript that encodes the protein. Regulatory RNA, such as siRNA, shRNA, short RNAs (typically less than 400 bases in length), micro-RNAs (miRNAs), ribozymes and decoy RNA, and antisense nucleic acids constitute exemplary functional nucleic acids.

"Gene" refers to a polynucleotide sequence that comprises control and coding sequences necessary for the production of a polypeptide or precursor. The polypeptide can be encoded by a full length coding sequence or by any portion of the coding sequence. A gene can constitute an uninterrupted coding sequence or it can include one or more introns, bound by the appropriate splice junctions. Moreover, a gene can contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. In this regard, such modified genes can be referred to as "variants" of the "native" gene.

"Host cell" refers to a cell that can be, or has been, used as a recipient for a recombinant plasmid or other transfer of polynucleotides, and includes the progeny of the original cell that has been transfected. The progeny of a single cell can not necessarily be completely identical in morphology or in genomic or total DNA complement as the original parent due to natural, accidental, or deliberate mutation.

"Hybridization" refers to any process by which a polynucleotide sequence binds to a complementary sequence through base pairing.

"Individual," "subject," "host," and "patient," used interchangeably in this description, refer to any mammalian subject for whom diagnosis, treatment, or therapy is desired. In one preferred embodiment, the individual, subject, host, or patient is a human. Other subjects can include but are not limited to cattle, horses, dogs, cats, guinea pigs, rabbits, rats, primates and mice.

"Label" refers to agents that are capable of providing a detectable signal, either directly or through interaction with one or more additional members of a signal producing system. Labels that are directly detectable and can find use in the invention include fluorescent labels. Specific fluorophores include fluorescein, rhodamine, BODIPY, cyanine dyes and the like. The invention also contemplates the use of radioactive isotopes, such as $^{35}$S, $^{32}$P, $^{3}$H, and the like as labels. Colorimetric labels such as colloidal gold or colored glass or plastic (e.g., polystyrene, polypropylene, latex) beads can also be utilized. For instance, see U.S. Pat. No. 4,366,241, U.S. Pat. No. 4,277,437, U.S. Pat. No. 4,275,149, U.S. Pat. No. 3,996,345, U.S. Pat. No. 3,939,350, U.S. Pat. No. 3,850,752, and U.S. Pat. No. 3,817,837.

"Oligonucleotide" refers to a polynucleotide comprising, for example, from about 10 nucleotides (nt) to about 1000 nt. Oligonucleotides for use in the invention are preferably from about 10 nt to about 150 nt. The oligonucleotide can be a naturally occurring oligonucleotide or a synthetic oligonucleotide. Oligonucleotides can be modified.

"Minicell" refers to anucleate forms of bacterial cells, engendered by a disturbance in the coordination, during binary fission, of cell division with DNA segregation. Minicells are distinct from other small vesicles that are generated and released spontaneously in certain situations and are not due to specific genetic rearrangements or episomal gene expression. In the context of this invention the minicells are intact since other "denuded" forms, such as spheroplasts, poroplasts, protoplasts, would leak the packaged functional nucleic acid and would not be therapeutically effective. The intact minicell membrane allows the payload to be retained within the minicell and is released intracellularly within the target host mammalian cell.

In this description, "modified" and "chemically modified" refer to oligonucleotides or polynucleotides with one or more chemical changes to the natural molecular structures of all or any of the bases, sugar moieties, and internucleoside phosphate linkages, as well as to molecules having added substitutions or a combination of modifications at these sites. The internucleoside phosphate linkages can be phosphodiester, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone internucleotide linkages, or 3'-3', 5'-3', or 5'-5' linkages, and combinations of such similar linkages. The phosphodiester linkage can be replaced with a substitute linkage, such as phosphorothioate, methylamino, methylphosphonate, phosphoramidate, and guanidine, and the ribose subunit of the polynucleotides also can be substituted (e.g., hexose phosphodiester; peptide nucleic acids). The modifications can be internal (single or repeated) or at the end(s) of the oligonucleotide molecule, and can include additions to the molecule of the internucleoside phosphate linkages, such as deoxyribose and phosphate modifications which cleave or crosslink to the opposite chains or to associated enzymes or other proteins. The terms "modified oligonucleotides" and "modified polynucleotides" also include oligonucleotides or polynucleotides comprising modifications to the sugar moieties (e.g., 3'-substituted ribonucleotides or deoxyribonucleotide monomers), any of which are bound together via 5' to 3' linkages.

The phrase "nucleic acid molecules" and the term "polynucleotides" denote polymeric forms of nucleotides of any length, either ribonucleotides or deoxynucleotides. They include single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of a polynucleotide can comprise sugars and phosphate groups (as can typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. A polynucleotide can comprise modified nucleotides, such as methylated nucleotides and nucleotide analogs, uracyl, other sugars, and linking groups such as fluororibose and thioate, and nucleotide branches. A polynucleotide can be modified further, such as by conjugation with a labeling component. Other types of modifications include caps, substitution of one or more of the naturally occurring nucleotides with an analog, and introduction of means for attaching the polynucleotide to proteins, metal ions, labeling components, other polynucleotides, or a solid support.

"Pharmaceutically acceptable" refers to physiological compatibility. A pharmaceutically acceptable carrier or excipient does not abrogate biological activity of the composition being administered, is chemically inert and is not toxic to the organism in which it is administered.

The qualifier "plasmid-free" connotes the absence of a construct, such as a plasmid or viral vector, for in situ expression of a functional nucleic acid.

"Polypeptide" and "protein," used interchangeably herein, refer to a polymeric form of amino acids of any length, which can include translated, untranslated, chemically modified, biochemically modified, and derivatized amino acids. A polypeptide or protein can be naturally occurring, recombinant, or synthetic, or any combination of these. Moreover, a polypeptide or protein can comprise a fragment of a naturally occurring protein or peptide. A polypeptide or protein can be a single molecule or can be a multi-molecular complex. In addition, such polypeptides or proteins can have modified peptide backbones. The terms include fusion proteins, including fusion proteins with a heterologous amino acid sequence, fusions with heterologous and homologous leader sequences, with or without N-terminal methionine residues, immunologically tagged proteins, and the like.

"Purified" refers to a compound that is removed from its natural environment and is at least about 60%, 65%, 70%, 75%, 80%, 85%, 90%, 91%, 92%, 93%, 94%, 95%, 96%, 97%, 98%, 99%, 99.9%, or 99.99% free from other components with which it is naturally associated.

"Regulatory RNA" denotes a category inclusive of RNAs that affect expression by RNA interference, suppression of gene expression, or another mechanism. Accordingly, in addition to shRNA, siRNA, miRNA, and antisense ssRNA, the category of regulatory RNAs includes ribozymes and decoy RNAs, inter alia.

"Ribozyme" refers to an RNA molecule having an enzymatic activity that can repeatedly cleave other RNA molecules in a nucleotide base sequence-specific manner.

"RNA interference" (RNAi) denotes a RNA-guided mechanism as described above, involving degradation of complementary or partially complementary target RNA, for sequence- or gene-specific regulation of gene expression (protein synthesis).

"Sequence identity" connotes a degree of similarity or complementarity. There can be partial identity or complete identity. A partially complementary sequence is one that at least partially inhibits an identical sequence from hybridizing to a target polynucleotide; it is referred to using the functional term "substantially identical" The inhibition of hybridization of the completely complementary sequence to the target sequence can be examined using a hybridization assay (Southern or Northern blot, solution hybridization, and the like) under conditions of low stringency. A substantially identical sequence or probe will compete for and inhibit the binding (i.e., the hybridization) of a completely identical sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding can be tested by the use of a second target sequence which lacks even a partial degree of complementarity (e.g., less than about 30% identity); in the absence of non-specific binding, the probe will not hybridize to the second non-complementary target sequence.

Another way of viewing sequence identity, in the context to two nucleic acid or polypeptide sequences, entails referencing residues in the two sequences that are the same when aligned for maximum correspondence over a specified region. As used herein, "percentage of sequence identity" means the value determined by comparing two optimally aligned sequences over a comparison window, wherein the portion of the polynucleotide sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

"Short interfering RNA" (siRNA) refers to double-stranded RNA molecules, generally, from about 10 to about 30 nucleotides long that are capable of mediating RNA interference (RNAi). In general, siRNA molecules have a capacity to reduce expression of a protein by directly interacting with a transcript that encodes the protein.

A "therapeutically effective" amount of functional nucleic acid is a dosage of the molecule in question, e.g., siRNA, miRNA or free shRNA, that invokes a pharmacological response when administered to a subject, in accordance with the present invention. In the context of the present invention, therefore, a therapeutically effective amount can be gauged by reference to the prevention or amelioration of an adverse condition or symptom associated with a disease or disorder, either in an animal model or in a human subject, when functional nucleic acid-packaged minicells are administered, as described in greater detail below. An amount that proves "therapeutically effective amount" in a given instance, for a particular subject, may not be effective for 100% of subjects similarly treated for the disease or condition under consideration, even though such dosage is deemed a "therapeutically effective amount" by skilled practitioners. The appropriate dosage in this regard also will vary as a function, for example, of the type, stage, and severity of the disease or condition to be affected. In any event, the present illustration of in vitro testing (Example 2) and in vivo testing (Examples 4, 5 and 6) according to the present invention, as well as of methodology for quantifying a minicell-delivered amount of an functional nucleic acid molecule (Example 3), when considered in light of the entire description, empower a person knowledgeable in pre-clinical and clinical testing of drug candidates to determine, through routine experimentation, the therapeutically effective amount of functional nucleic acid for a particular indication.

The terms "treatment," "treating," "treat," and the like refer to obtaining a desired pharmacological and/or physiologic effect. The effect can be prophylactic in terms of completely or partially preventing a disease or symptom thereof and/or can be therapeutic in terms of a partial or complete stabilization or cure for a disease and/or adverse effect attributable to the disease. "Treatment" covers any treatment of a disease in a mammal, particularly a human, and includes: (a) preventing the disease or symptom from occurring in a subject which can be predisposed to the disease or symptom but has not yet been diagnosed as having it; (b) inhibiting the disease symptom, i.e., arresting its development; or (c) relieving the disease symptom, i.e., causing regression of the disease or symptom.

Minicells

Minicells of the invention are anucleate forms of E. coli or other bacterial cells, engendered by a disturbance in the coordination, during binary fission, of cell division with DNA segregation. Prokaryotic chromosomal replication is linked to normal binary fission, which involves mid-cell septum formation. In E. coli, for example, mutation of min genes, such as minCD, can remove the inhibition of septum formation at the cell poles during cell division, resulting in production of a normal daughter cell and an anucleate minicell. See de Boer et al., 1992; Raskin & de Boer, 1999; Hu & Lutkenhaus, 1999; Harry, 2001. Minicells are distinct from other small vesicles that are generated and released spontaneously in certain situations and, in contrast to minicells, are not due to specific genetic rearrangements or episomal gene expression. In a preferred embodiment, minicells possess intact cell walls ("intact minicells").

In addition to min operon mutations, anucleate minicells also are generated following a range of other genetic rearrangements or mutations that affect septum formation, for example in the divIVB1 in B. subtilis. See Reeve and Cornett, 1975. Minicells also can be formed following a perturbation in the levels of gene expression of proteins involved in cell division/chromosome segregation. For example, overexpression of minE leads to polar division and production of minicells. Similarly, chromosome-less minicells can result from defects in chromosome segregation for example the smc mutation in Bacillus subtilis (Britton et al., 1998), spoOJ deletion in B. subtilis (Ireton et al., 1994), mukB mutation in E. coli (Hiraga et al., 1989), and parC mutation in E. coli (Stewart and D'Ari, 1992). Gene products can be supplied in trans. When over-expressed from a high-copy number plasmid, for example, CafA can enhance the rate of cell division and/or inhibit chromosome partitioning after replication (Okada et al., 1994), resulting in formation of chained cells and anucleate minicells (Wachi et al., 1989). Minicells can be prepared from any bacterial cell of Gram-positive or Gram-negative origin.

In one aspect, minicells can contain one or more plasmid-free functional nucleic acid for which delivery is desired. Functional nucleic acid of the invention have the capacity to reduce expression of a protein by directly interacting with a transcript that encodes the protein.

Packaging Functional Nucleic Acid into Intact Minicells

Functional nucleic acid can be packaged directly into intact minicells. The process bypasses the previously required steps of, for example, cloning nucleic acids encoding functional nucleic acid into expression plasmids, transforming minicell-producing parent bacteria with the plasmids and generating recombinant minicells. Instead, plasmid-free functional nucleic acid can be packaged directly into intact minicells by co-incubating a plurality of intact minicells with functional nucleic acid in a buffer. In some embodiments, the co-incubation may involve gentle shaking, while in others the co-incubation is static. A co-incubation period of about one hour has proven sufficient, but shorter periods, such as about half an hour, also may be effective. In one embodiment, the buffer comprises buffered saline, for example a 1× phosphate buffer solution. The buffered saline can be in gelatin form. In another embodiment, the co-incubation is conducted at a temperature of about 4° C. to about 37° C.; about 20° C. to about 30° C.; about 25° C.; or about 37° C. In other aspects, the co-incubation can comprise about $10^7$, $10^8$, $10^9$, $10^{10}$, $10^{11}$, $10^{12}$ or $10^{13}$ minicells. Specific parameters of temperature, time, buffer, minicell concentration, etc. can be optimized for a particular combination of conditions.

The success of this approach is startling because, for over four decades, practitioners have developed a variety of chemical and electrochemical processes (reviewed by Miller, 1994) to transform nucleic acids into bacterial cells. Practitioners have utilized such harsh measures because conventional wisdom has held that nucleic acids such as siRNA, miRNA or plasmid-free shRNA are too large to passively enter into the minicell cytoplasm. For example, porins, which are β-barrel proteins that typically function as diffusion pores, permit passive transport across the bacterial outer membrane of molecules with molecular weights of 600 daltons or less (Nikaido, 1994). Meanwhile, double stranded plasmid DNA encoding shRNA exceeds a million daltons, and double stranded siRNA or miRNA exceeds 15,000 daltons.

Moreover, once packaged, the functional nucleic acid remain inside the minicell and are protected from degradation. In this regard, prolonged incubation studies with siRNA-packaged minicells incubated in sterile saline showed no leakage of siRNAs. In addition, co-incubating siRNA-packaged minicells with nucleases confirmed that the siRNAs had penetrated the outer membrane of the intact minicells and were protected from degradation. Similarly, despite the fact that minicells might be expected to carry residual nucleases from the parent bacterial cytoplasm, packaged siRNA are stable in the minicell cytoplasm. Packaged siRNA also avoid the degradative machinery present within phagolysosomes, such as acids, free oxygen radicals and acid hydrolases (Conner and Schmid, 2003), to effect target mRNA knockdown within the mammalian cell.

In other embodiments, multiple functional nucleic acids directed to different mRNA targets can be packaged in the same minicell. Such an approach can be used to combat drug resistance and apoptosis resistance. For example, cancer patients routinely exhibit resistance to chemotherapeutic drugs. Such resistance can be mediated by over-expression of genes such as multi-drug resistance (MDR) pumps and anti-apoptotic genes, among others. To combat this resistance, minicells can be packaged with therapeutically significant concentrations of functional nucleic acid to MDR-associated genes and administered to a patient before chemotherapy. Furthermore, packaging into the same minicell multiple functional nucleic acid directed to different mRNA targets can enhance therapeutic success since most molecular targets are subject to mutations and have multiple alleles.

Thus, packaging plasmid-free functional nucleic acid directly into intact minicells, as described here, offers numerous advantages. For example, since the inventive approach does not require genetically modifying parent bacteria to accommodate expression of functional nucleic acid, one parent bacteria can be used to produce minicells comprising many types of nucleic acids, directed to a variety of indications. Similarly, a minicell can be loaded with a variety of different RNAs, thereby to avoid or overcome resistance mechanisms.

Functional Nucleic Acids

As noted above, functional nucleic acid denotes a category inclusive of nucleic acid molecules that affect expression by RNA interference, suppression of gene expression, or another mechanism. Such molecules are exemplified by single-, double-, or multi-stranded DNA or RNA. Examples of functional nucleic acids include, but are not limited to regulatory RNA, such as shRNA, siRNA, miRNA, and antisense ssRNA, therefore, ribozymes and decoy RNAs and antisense nucleic acids.

In a preferred embodiment of the invention, the intact minicells carry siRNA molecules. Short interfering RNA molecules are useful for performing RNAi, a post-transcriptional gene silencing mechanism. As noted, "siRNA" generally refers to double-stranded RNA molecules from about 10 to about 30 nucleotides long that are named for their ability specifically to interfere with protein expression. Preferably, siRNA molecules are 12-28 nucleotides long, more preferably 15-25 nucleotides long, still more preferably 19-23 nucleotides long and most preferably 21-23 nucleotides long. Therefore, preferred siRNA molecules are 12, 13, 14, 15, 16, 17, 18, 19, 20, 21, 22, 23, 24, 25, 26, 27 28 or 29 nucleotides in length.

The length of one strand designates the length of an siRNA molecule. For instance, an siRNA that is described as 21 ribonucleotides long (a 21-mer) could comprise two opposite strands of RNA that anneal together for 19 contiguous base pairings. The two remaining ribonucleotides on each strand would form an "overhang." When an siRNA contains two strands of different lengths, the longer of the strands designates the length of the siRNA. For instance, a dsRNA containing one strand that is 21 nucleotides long and a second strand that is 20 nucleotides long, constitutes a 21-mer.

siRNAs that comprise an overhang are desirable. The overhang can be at the 5' or the 3' end of a strand. Preferably, it is at the 3' end of the RNA strand. The length of an overhang can vary, but preferably is about 1 to about 5 bases, and more preferably is about 2 nucleotides long. Preferably, the siRNA of the present invention will comprise a 3' overhang of about 2 to 4 bases. More preferably, the 3' overhang is 2 ribonucleotides long. Even more preferably, the 2 ribonucleotides comprising the 3' overhang are uridine (U).

shRNAs comprise a single strand of RNA that forms a stem-loop structure, where the stem consists of the complementary sense and antisense strands that comprise a double-stranded siRNA, and the loop is a linker of varying size. The stem structure of shRNAs generally is from about 10 to about 30 nucleotides long. Preferably, the stem of shRNA molecules are 12-28 nucleotides long, more preferably 15-25 nucleotides long, still more preferably 19-23 nucleotides long and most preferably 21-23 nucleotides long. Therefore, preferred shRNA molecules comprise stems that are 12, 13, 14, 15, 16, 17, 18, 19, 20, 21, 22, 23, 24, 25, 26, 27 28 or 29 nucleotides in length.

siRNAs of the invention are designed to interact with a target ribonucleotide sequence, meaning they complement a target sequence sufficiently to hybridize to the target sequence. In one embodiment, the invention provides an siRNA molecule comprising a ribonucleotide sequence at least 70%, 75%, 80%, 85% or 90% identical to a target ribonucleotide sequence or the complement of a target ribonucleotide sequence. Preferably, the siRNA molecule is at least 90%, 95%, 96%, 97%, 98%, 99% or 100% identical to the target ribonucleotide sequence or the complement of the target ribonucleotide sequence. Most preferably, an siRNA will be 100% identical to the target nucleotide sequence or the complement of the ribonucleotide sequence. However, siRNA molecules with insertions, deletions or single point mutations relative to a target also can be effective.

Accordingly, in one aspect of the invention, intact minicells can carry one or more siRNA sequences aimed at silencing drug resistance or apoptosis resistance genes. Using minicells that encode multiple siRNAs, it is possible to treat cells that express multiple drug resistance mechanisms.

Tools to assist siRNA design, and regulatory RNA in general, are readily available to the public. For example, a computer-based siRNA design tool is available on the internet at www.dharmacon.com.

Targets of Functional Nucleic Acid

Functional nucleic acid of the invention target the gene or transcript of a protein that promotes drug resistance, inhibits apoptosis, promotes a neoplastic phenotype, inhibits pathogen proliferation or inhibits viral replication or proliferation. Successful application of functional nucleic acid strategies in these contexts have been achieved in the art, but without the benefits of minicell vectors. See, e.g., Sioud (2004), Caplen (2003), Wu et al. (2003), Yague et al. (2004).

Proteins that contribute to drug resistance or promotion of neoplastic phenotype constitute preferred targets of functional nucleic acid. The proteins can contribute to acquired drug resistance or intrinsic drug resistance. When diseased cells, such as tumor cells, initially respond to drugs, but become refractory on subsequent treatment cycles, the resistant phenotype is acquired. Useful targets involved in acquired or intrinsic drug resistance include but not limited to ATP binding cassette transporters such as P-glycoprotein (P-gp, P-170, PGY1, MDR1, ABCB1, MDR-associated protein, Multidrug resistance protein 1, MDR-2 and MDR-3, MRP2 (multi-drug resistance associated protein), BCR-ABL (breakpoint cluster region—Abelson protooncogene), STI-571 resistance-associated protein, lung resistance-related protein, cyclooxygenase-2, nuclear factor kappa, XRCC1 (X-ray cross-complementing group 1), ERCC1 (Excision cross-complementing gene), GSTP1 (Glutathione S-transferase), mutant β-tubulin, Abcb1a (ABCB4), Abcc1, Abcc2, Abcc3 (MLP-2), Abcc5, Abcc6, Abcd2, Abcg2, Bax, Bcl2, Bcl21 (bcl-x), Mvp, Rb1, Top1, Top2a, Top2b, Trp53 (p53). Other genes involved in drug resistance also include (a) genes involved in drug metabolism for example Arnt, Blmh, C130052I12Rik (CRR9p), Comt, Crabp1, Cyp1a1, Cyp1a2, Cyp2b19, Cyp2b20, Cyp2c29, Cyp2c40, Cyp2c70, Cyp2d22, Cyp2e1, Dhfr, Ephx1, Ephx2, Gstm1 (MGST1), Gstp1, Nat2, Nqo1, Sod1, Ste, Tpmt, Tyms, Ugcg, (b) genes involved in DNA repair for example Apc, Atm, Brca1, Brca2, Ercc3 (XPB), Mgmt, Mlh1, Xpa, Xpc, (c) genes involved in cell cycle for example Ccnd1 (cyclin D1), Ccne1 (cyclin E1), Cdk1, Cdk2, Cdk4, Cdkn1a (p21Waf1), Cdkn1b (p27Kip1), Cdkn2a (p16Ink4a), Cdkn2d (p19), KSP, (d) genes involved in growth factor receptors for example Egfr, Erbb2 (Neu, HER2), Erbb3, Erbb4, Fgf2 (bFGF), Met, (e) genes involved in hormone receptors for example Ar, Esr1, Esr2, Igf2r, Ppara, Ppard, Pparg, Ppargc1, Rara, Rarb, Rxra, Rxrb, Rxrg, Srd5a2, and (f) genes involved in transcription factors for example Ahr, Ap1s1, Ap1s2, Elk1, Fos (c-fos), Gabpa, Hif1a, Math, Myc (c-myc), Nfkb1, Nfkb2, Nfkbib, Nfkbie, Relb (1-rel), Tnfrsf11A.

Useful targets also include proteins that contribute to apoptosis resistance. These include Bcl-2 (B cell leukemia/lymphoma), Bcl-$X_L$, A1/Bfl 1, focal adhesion kinase and p53 mutant protein.

Useful targets further include oncogenic and mutant tumor suppressor proteins. Examples include β-Catenin, PKC-α (protein kinase C), C-RAF, K-Ras (V12), h-Ras, DP97 Dead box RNA helicase, DNMT1 (DNA methyltransferase 1), FLIP (Flice-like inhibitory protein), C-Sfc, 53BPI, Polycomb group protein EZH2 (Enhancer of zeste homologue), ErbB1, HPV-16 E5 and E7 (human papillomavirus early 5 and early 7), Fortilin & MCI1P (Myeloid cell leukemia 1 protein), DIP13α(DDC interacting protein 13a), MBD2 (Methyl CpG binding domain), p21, KLF4 (Kruppel-like factor 4), tpt/TCTP (Translational controlled tumor protein), SPK1 & SPK2 (Sphingosine kinase), P300, PLK1 (Polo-like kinase-1), Trp53, Ras, ErbB1, VEGF (Vascular endothelial growth factor), and BAG-1 (BCL2-associated athanogene 1).

A large number of molecular targets have been identified for the treatment of cancer, and RNAi discovery platforms are rapidly identifying a range of different new targets. Examples of such molecular targets useful in this invention include, tyrosine kinase (variant), Akt (protein kinase B, PKB), Akt1, AlphaLbeta2 integrin, Aminopeptidase, Androgen receptor, Aurora A, AuroraB, Basic fibroblast growth factor (bFGF) receptor (bFGFr), BRaf, Carcinoembryonic antigen (CEA), CD142, CD37, CD44, CD5, CD74, CD77, Chk1, CHK2, CHras, CSF1r, CXCR4, Cyclin D1 (CCND1), Cyclin-dependent kinase 1 (CDK1), Cyclin dependent kinase 2 (CDK2), Cyclin-dependent kinase inhibitor 1B (CDKN1B, p27, KIP1), CYP26, Fibroblast growth factor receptor 3 (FGFr3), Fibroblast growth factor receptor 4 (FGFr4), G250, Hedgehog (Hh) signaling pathway, Hepatocyte growth factor/scatter factor (HGF/SF or SF/HGF), HEr4 (ErbB4), HIF, Histone deacetylase 9 (HDAC9), Homeobox gene (HOXB7), Hyaluronan (HA), Insulin like growth factor (IGF), Insulin like growth factor 1 receptor (IGF1r, IGF1r, IGFIr, IGFIr), Insulin like growth factor binding protein 2 (IGFBP2), Insulin like growth factor binding protein 5 (IGFBPS), Integrin like kinase (ILK) Interleukin (IL6) receptor, Interleukin 1 (IL1) receptor type II, Interleukin 10 (IL10), Interleukin 4 (IL4) receptor, Interleukin 6 (IL6), Interleukin15 (IL15), Interleukin3 receptor alpha (IL3r alpha) chain, JAK, JAK3, JNK1, JNK2, Kinesin Spindle Protein (KSP), Laminin 5, Lewis (b), Lymphotoxin (LT) beta receptor (LTBr), Lysophosphatidic acid (LPA) receptors (LPAr), Lysophosphatidic acid acyltransferase, Macrophage migration inhibitory factor (MIF), MAGE3, Microtubules, MUC2, Notch 1 (TAN1), P38 mitogen activated protein kinase (p38 MAPK), P53 upregulated mediator of apoptosis (PUMA), PDGF tyrosine kinase (TK) signaling pathway, Phosphatase and tensin homolog (PTEN), Phosphatidylinositol 3'kinase (PI3K), Plasminogen activator, urokinase (PLAU) receptor (PLAUr), Pololike kinase 1 (Plk1), Poly (ADP ribose), polymerase (PARP), Proliferating cell nuclear antigen (PCNA), Prostate stem cell antigen (PSCA), Prostate specific antigen (PSA) 773, Protein tyrosine phosphatase (PTP), Rad51 protein, RAF1, Retinoic acid receptor (RAr) alpha, Retinoic acid receptor (RAr) gamma, Retinoid X receptor (RXr) beta, Serine (or cysteine) proteinase inhibitor, Telomerase reverse transcriptase (TERT, hTERT), Telomeres, Thomsen Friedenreich (TF) antigen, Thrombospondin1 (TSP1), Transferrin, Tumor necrosis factor alpha (TNFa, TNFA), Tumor necrosis factor receptor (TNFr, TNFr), Tumor associated carbonic anhydrase (CA) IX (CA9), Type I interferon, Ubiquitin ligase, Vascular cell adhesion molecule 1 (VCAM1, CD106), Vascular endothelial growth factor (VEGF, VEGFA), Vascular endothelial growth factor D (VEGFD), Vitronectin (VTN), Wilms' tumor 1 (WT1) etc.

With regard to HIV infection, targets include HIV-Tat, HIV-Rev, HIV-Vif, HIV-Nef, HIV-Gag, HIV-Env, LTR, CD4, CXCR4 (chemokine receptor) and CCRS (chemokine receptor).

Because of tumor cell heterogeneity, a number of different drug resistance or apoptosis resistance pathways can be operational in target cells. Therefore, the functional nucleic acid used in methods of the invention can require change over time. For instance, if biopsy samples reveal new mutations that result in acquired drug resistance, specific functional nucleic acid can be designed and packaged into intact minicells that are administered to the mammalian host to address the acquired drug resistance.

Delivery of Functional Nucleic Acid Via Intact Minicells

In a second aspect, the invention provides a method of delivering functional nucleic acid, comprising (a) providing a plurality of intact minicells in a pharmaceutically acceptable carrier, each minicell of the plurality encompassing plasmid-free functional nucleic acid, and (b) bringing minicells of the plurality into contact with mammalian cells such that the mammalian cells engulf minicells of the plurality, whereby the functional nucleic acid is released into the cytoplasm of the target cells. Minicells are brought into contact with the target mammalian cell via bispecific ligands as described in published PCT application WO 05/056749. Contact between the minicell and the target mammalian cell can be in vitro or in vivo.

Method of Overcoming Drug Resistance and Treating Disease

In another aspect, the invention provides a method of overcoming drug resistance and treating a disease, such as cancer or AIDS, in a subject. The method comprises (a) packaging one or more functional nucleic acid that target genes or transcripts of proteins that promote drug resistance into intact purified minicells, (b) bringing the functional nucleic acid containing minicells into contact with a target mammalian cell, such that the mammalian cell engulfs the minicell, as described in the above-cited '749 PCT application, which is hereby incorporated by reference, and (c) delivering a drug to the target mammalian cell, as described in published PCT application WO 05/079854. Preferably, step (c) is performed after steps (a) and (b), to allow the functional nucleic acid to diminish resistance to the drug prior to the drug's administration. Delivery of the drug and introduction of the functional nucleic acid can occur consecutively, in any order, or simultaneously.

According to the invention, drugs can be delivered by any conventional means. For example, drugs can be delivered orally, parenterally (including subcutaneously, intravenously, intramuscularly, intraperitoneally, and by infusion), topically, transdermally or by inhalation. The appropriate mode of delivery and dosage of each drug is easily ascertainable by those skilled in the medical arts.

Drug Delivery Via Minicells

Although drug delivery can occur via conventional means, delivery via minicells is preferred, as described in published PCT application WO 05/079854, which is hereby incorporated by reference. In this regard, the inventors have discovered that the same mammalian cells can be successfully re-transfected by targeted intact minicells that are packaged with different payloads. For example, functional nucleic acid-packaged minicells can transfect a mammalian cell, after which drug-packaged minicells can deliver drug to the same mammalian cell to obtain a complementary or synergistic anti-tumor effect.

The drug can be packaged in a separate minicell from the functional nucleic acid. Alternatively, the drug can be packaged in the same minicell as the functional nucleic acid. Certain drugs can interact with nucleic acids and preclude co-packaging of drug and nucleic acid in the same minicell. For example, Doxorubicin is known to interact with DNA.

Preferably, minicells of the invention contain a sufficient quantity of drug to exert the drug's physiological or pharmacological effect on a target cell. Also preferably, drugs contained within the minicells are heterologous, or foreign, to the minicells, meaning that the minicells' parent bacterial cells do not normally produce the drug.

Both hydrophilic and hydrophobic drugs can be packaged in minicells by creating a concentration gradient of the drug between an extracellular medium containing minicells and the minicell cytoplasm. When the extracellular medium contains a higher drug concentration than the minicell cytoplasm, the drug naturally moves down this concentration gradient, into the minicell cytoplasm. When the concentration gradient is reversed, however, the drug does not move out of the minicells. The procedure and mechanisms for drug loading into minicells is as described in published PCT application WO 05/079854.

To load minicells with drugs that normally are not water soluble, the drugs initially can be dissolved in an appropriate solvent. For example, Paclitaxel can be dissolved in a 1:1 blend of ethanol and cremophore EL (polyethoxylated castor oil), followed by a dilution in PBS to achieve a solution of Paclitaxel that is partly diluted in aqueous media and carries minimal amounts of the organic solvent to ensure that the drug remains in solution. Minicells can be incubated in this final medium for drug loading. Thus, the inventors discovered that even hydrophobic drugs can diffuse into the cytoplasm of minicells to achieve a high and therapeutically significant cytoplasmic drug load. This is unexpected because the minicell membrane is composed of a hydrophobic phospholipid bilayer, which would be expected to prevent diffusion of hydrophobic molecules into the cytoplasm.

Another method of loading minicells with a drug involves culturing a recombinant parent bacterial cell under conditions such that the parent bacterial cell transcribes and translates a nucleic acid encoding the drug, and the drug is released into the cytoplasm of the parent bacterial cell. For example, a gene cluster encoding the cellular biosynthetic pathway for a desired drug can be cloned and transferred into a parent bacterial strain that is capable of producing minicells. Genetic transcription and translation of the gene cluster results in biosynthesis of the drug within the cytoplasm of the parent bacterial cells, filling the bacterial cytoplasm with the drug. When the parent bacterial cell divides and forms progeny minicells, the minicells also contain the drug in their cytoplasm. The pre-packaged minicells can be purified by any suitable minicell-purification process, including the methodology described above.

Similarly, another method of loading minicells with a drug involves culturing a recombinant minicell that contains an expression plasmid encoding the drug under conditions such that the gene encoding the drug is transcribed and translated within the minicell.

Drugs

Drugs useful in the invention can be any physiologically or pharmacologically active substance that produces a desired local or systemic effect in animals, particularly mammals and humans. Drugs can be inorganic or organic compounds, without limitation, including peptides, proteins, nucleic acids, and small molecules, any of which can be characterized or uncharacterized. They can be in various forms, such as unchanged molecules, molecular complexes, pharmacologically acceptable salts, such as hydrochloride, hydrobromide, sulfate, laurate, palmitate, phosphate, nitrite, nitrate, borate, acetate, maleate, tartrate, oleate, salicylate, and the like. For acidic drugs, salts of metals, amines or organic cations, for example, quaternary ammonium, can be used. Derivatives of drugs, such as bases, esters and amides also can be used. A drug that is water insoluble can be used in a form that is a water soluble derivative thereof, or as a base derivative thereof, which in either instance, or by its delivery, is converted by enzymes, hydrolyzed by the body pH, or by other metabolic processes to the original therapeutically active form.

Useful drugs include chemotherapeutic agents, immunosuppressive agents, cytokines, cytotoxic agents, nucleolytic compounds, radioactive isotopes, receptors, and pro-drug activating enzymes, which can be naturally occurring or produced by recombinant methods.

Drugs that are affected by classical multidrug resistance have particular utility in the invention, such as vinca alkaloids (e.g., vinblastine and vincristine), the anthracyclines (e.g., doxorubicin and daunorubicin), RNA transcription inhibitors (e.g., actinomycin-D) and microtubule stabilizing drugs (e.g., paclitaxel).

In general, cancer chemotherapy agents are preferred drugs. Useful cancer chemotherapy drugs include nitrogen mustards, nitrosoruueas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, Melphalan, Mercaptopurine, Methotrexate, Mitomycin, Mitotane, Mitoxantrone, Oxaliplatin, Paclitaxel, Pamidronate, Pentostatin, Plicamycin, Procarbazine, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Vinblastine, Vincristine, Vindesine, Vinorelbine, VP-16, and Xeloda.

Useful cancer chemotherapy drugs also include alkylating agents such as Thiotepa and cyclosphosphamide; alkyl sulfonates such as Busulfan, Improsulfan and Piposulfan; aziridines such as Benzodopa, Carboquone, Meturedopa, and Uredopa; ethylenimines and methylamelamines including altretamine, triethylenemelamine, trietylenephosphoramide, triethylenethiophosphaoramide and trimethylolomelamine; nitrogen mustards such as Chlorambucil, Chlornaphazine, Cholphosphamide, Estramustine, Ifosfamide, mechlorethamine, mechlorethamine oxide hydrochloride, Melphalan, Novembiehin, Phenesterine, Prednimustine, Trofosfamide, uracil mustard; nitroureas such as Cannustine, Chlorozotocin, Fotemustine, Lomustine, Nimustine, and Ranimustine; antibiotics such as Aclacinomysins, Actinomycin, Authramycin, Azaserine, Bleomycins, Cactinomycin, Calicheamicin, Carabicin, Carminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin; antimetabolites such as Methotrexate and 5-fluorouracil (5-FU); folic acid analogues such as Denopterin, Methotrexate, Pteropterin, and Trimetrexate; purine analogs such as Fludarabine, 6-mercaptopurine, Thiamiprine, and Thioguanine; pyrimidine analogs such as Ancitabine, Azacitidine, 6-azauridine, Carmofur, Cytarabine, Dideoxyuridine, Doxifluridine, Enocitabine, Floxuridine, and 5-FU; androgens such as Calusterone, Dromostanolone Propionate, Epitiostanol, Rnepitiostane, and Testolactone; anti-adrenals such as aminoglutethimide, Mitotane, and Trilostane; folic acid replenisher such as frolinic acid; aceglatone; aldophosphamide glycoside; aminolevulinic acid; Amsacrine; Bestrabucil; Bisantrene; Edatraxate; Defofamine; Demecolcine; Diaziquone; Elfornithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK®; Razoxane; Sizofrran; Spirogermanium; tenuazonic acid; triaziquone; 2,2',2"-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide; thiotEPa; taxoids, e.g., Paclitaxel (TAXOL®, Bristol-Myers Squibb Oncology, Princeton, N.J.) and Doxetaxel (TAXOTERE®, Rhone-Poulenc Rorer, Antony, France); Chlorambucil; Gemcitabine; 6-thioguanine; Mercaptopurine; Methotrexate; platinum analogs such as Cisplatin And Carboplatin; Vinblastine; platinum; etoposide (VP-16); Ifosfamide; Mitomycin C; Mitoxantrone; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylornithine (DMFO); retinoic acid; Esperamicins; Capecitabine; and pharmaceutically acceptable salts, acids or derivatives of any of the above. Also included are anti-hormonal agents that act to regulate or inhibit hormone action on tumors such as anti-estrogens including for example Tamoxifen, Raloxifene, aromatase inhibiting 4(5)-imidazoles, 4 Hydroxytamoxifen, Trioxifene, Keoxifene, Onapristone, And Toremifene (Fareston); and anti-androgens such as Flutamide, Nilutamide, Bicalutamide, Leuprolide, and Goserelin; and pharmaceutically acceptable salts, acids or derivatives of any of the above.

Useful drugs also include cytokines. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet growth factor; transforming growth factors (TGFs) such as TGF-α and TGF-β; insulin-like growth factor-I and -II; erythropoietin (EPO); osteoinductive factors; interferons such as interferon-α, -β and -γ; colony stimulating factors (CSFs) such as macrophage-CSF (M-CSF); granulocyte-macrophage-CSF (GM-CSF); and granulocyte-CSF (GCSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-α or TNF-β; and other polypeptide factors including LIF and kit ligand (KL). As used herein, the tern cytokine includes proteins from natural sources or from recombinant cell culture and biologically active equivalents of the native sequence cytokines.

The drugs can be prodrugs, subsequently activated, e.g., by a prodrug-activating enzyme that converts a prodrug, such as a peptidyl chemotherapeutic agent, to an active anti-cancer drug. For instance, see WO 88/07378, WO 81/01145, and U.S. Pat. No. 4,975,278. In general, the enzyme component includes any enzyme capable of acting on a prodrug in such a way so as to covert it into its more active, cytotoxic form.

Directing Minicells to Specific Mammalian Cells

In one aspect of the invention, a minicell is directed to a target mammalian cell via a bispecific ligand as described in published PCT applications WO 05/056749 and WO 05/079854. The bispecific ligand, having specificity for both minicell and mammalian cell components, causes the minicell to bind to the mammalian cell, such that the minicell is engulfed by the mammalian cell, whereby functional nucleic acid is released into the cytoplasm of the mammalian cell. This targeted delivery method can be performed in vivo or in vitro, or both in vivo and in vitro.

Contact between bispecific ligand, minicell and mammalian cell can occur in a number of different ways. For in vivo delivery, it is preferable to administer a minicell that already has the bispecific ligand attached to it. Thus, minicell, bispecific ligand and target cell all are brought into contact when the bispecific ligand-targeted minicell reaches the target cell in vivo. Alternatively, bispecific ligand and minicell can be separately administered in vivo.

Contact between the bispecific ligands, minicells and mammalian cells also can occur during one or more incubations in vitro. In one embodiment, the three elements are incubated together all at once. Alternatively, step-wise incubations can be performed. In one example of a step-wise approach, minicells and bi-specific ligands are first incubated together to form bispecific ligand-targeted minicells, which are then incubated with target cells. In another example, bispecific ligands are first incubated with target cells, followed by an incubation with minicells. A combination of one or more in vitro incubations and in vivo administrations also can bring bispecific ligands, minicells and mammalian target cells into contact.

The inventors found that the targeted delivery approach is broadly applicable to a range of mammalian cells, including cells that normally are refractory to specific adhesion and endocytosis of minicells. For example, bispecific antibody ligands with anti-O-polysaccharide specificity on one arm and anti-HER2 receptor or anti-EGF receptor specificity on the other arm efficiently bind minicells to the respective receptors on a range of target non-phagocytic cells. These cells include lung, ovarian, brain, breast, prostate and skin cancer cells. Moreover, the efficient binding precedes rapid endocytosis of the minicells by each of the non-phagocytic cells.

Target cells of the invention include any cell into which a functional nucleic acid is to be introduced. Desirable target cells are characterized by expression of a cell surface receptor that, upon binding of a ligand, facilitates endocytosis. Preferred target cells are non-phagocytic, meaning that the cells are not professional phagocytes, such as macrophages, dendritic cells and Natural Killer (NK) cells. Preferred target cells also are mammalian.

Ligands useful in the targeted delivery methods of this invention include any agent that binds to a surface component on a target cell and to a surface component on a minicell. Preferably, the surface component on a target cell is a receptor, especially a receptor capable of mediating endocytosis. The ligands can comprise a polypeptide and/or carbohydrate component. Antibodies are preferred ligands. For example, a bispecific antibody that carries dual specificities for a surface component on bacterially derived intact minicells and for a surface component on target mammalian cells, can be used efficiently to target the minicells to the target mammalian cells in vitro and in vivo. Useful ligands also include receptors, enzymes, binding peptides, fusion/chimeric proteins and small molecules.

The selection of a particular ligand is made on two primary criteria: (i) specific binding to one or more domains on the surface of intact minicells and (ii) specific binding to one or more domains on the surface of the target cells. Thus, ligands preferably have a first arm that carries specificity for a bacterially derived intact minicell surface structure and a second arm that carries specificity for a mammalian cell surface structure. Each of the first and second arms can be multivalent. Preferably, each arm is monospecific, even if multivalent.

For binding to bacterially derived minicells, it is desirable for one arm of the ligand to be specific for the O-polysaccharide component of a lipopolysaccharide found on the parent bacterial cell. Other minicell surface structures that can be exploited for ligand binding include cell surface-exposed polypeptides and carbohydrates on outer membranes, such as outer-membrane proteins, pilli, fimbrae and flagella cell surface exposed peptide segments.

For binding to target cells, one arm of the ligand is specific for a surface component of a mammalian cell. Such components include cell surface proteins, peptides and carbohydrates, whether characterized or uncharacterized. Cell surface receptors, especially those capable of activating receptor-mediated endocytosis, are desirable cell surface components for targeting. Such receptors, if over-expressed on the target cell surface, confer additional selectivity for targeting the cells to be treated, thereby reducing the possibility for delivery to non-target cells.

By way of example, one can target tumor cells, metastatic cells, vasculature cells, such as endothelial cells and smooth muscle cells, lung cells, kidney cells, blood cells, bone marrow cells, brain cells, liver cells, and so forth, or precursors of any selected cell by selecting a ligand that specifically binds a cell surface receptor motif on the desired cells. Examples of cell surface receptors include carcinoembryonic antigen (CEA), which is overexpressed in most colon, rectum, breast, lung, pancreas and gastrointestinal tract carcinomas (Marshall, 2003); heregulin receptors (HER-2, neu or c-erbB-2), which is frequently overexpressed in breast, ovarian, colon, lung, prostate and cervical cancers (Hung et al., 2000); epidermal growth factor receptor (EGFR), which is highly expressed in a range of solid tumors including those of the breast, head and neck, non-small cell lung and prostate (Salomon et al., 1995); asialoglycoprotein receptor (Stockert, 1995); transferrin receptor (Singh, 1999); serpin enzyme complex receptor, which is expressed on hepatocytes (Ziady et al., 1997); fibroblast growth factor receptor (FGFR), which is overexpressed on pancreatic ductal adenocarcinoma cells (Kleeff et al., 2002); vascular endothelial growth factor receptor (VEGFR), for anti-angiogenesis gene therapy (Becker et al., 2002; Hoshida et al., 2002); folate receptor, which is selectively overexpressed in 90% of nonmucinous ovarian carcinomas (Gosselin and Lee, 2002); cell surface glycocalyx (Batra et al., 1994); carbohydrate receptors (Thurnher et al., 1994); and polymeric immunoglobulin receptor, which is useful for gene delivery to respiratory epithelial cells and attractive for treatment of lung diseases such as Cystic Fibrosis (Kaetzel et al., 1997).

Preferred ligands comprise antibodies and/or antibody derivatives. As used herein, the term "antibody" encompasses an immunoglobulin molecule obtained by in vitro or in vivo generation of an immunogenic response. The term "antibody" includes polyclonal, monospecific and monoclonal antibodies, as well as antibody derivatives, such as single-chain antibody fragments (scFv). Antibodies and antibody derivatives useful in the present invention also can be obtained by recombinant DNA techniques.

Wild-type antibodies have four polypeptide chains, two identical heavy chains and two identical light chains. Both types of polypeptide chains have constant regions, which do not vary or vary minimally among antibodies of the same class, and variable regions. Variable regions are unique to a particular antibody and comprise an antigen binding domain that recognizes a specific epitope. The regions of the antigen binding domain that are most directly involved in antibody binding are "complementarity-determining regions" (CDRs).

The term "antibody" also encompasses derivatives of antibodies, such as antibody fragments that retain the ability to specifically bind to antigens. Such antibody fragments include Fab fragments (a fragment that contains the antigen-binding domain and comprises a light chain and part of a heavy chain bridged by a disulfide bond), Fab' (an antibody fragment containing a single antigen-binding domain comprising a Fab and an additional portion of the heavy chain through the hinge region, F(ab')2 (two Fab' molecules joined by interchain disulfide bonds in the hinge regions of the heavy chains), a bispecific Fab (a Fab molecule having two antigen binding domains, each of which can be directed to a different epitope), and an scFv (the variable, antigen-binding determinative region of a single light and heavy chain of an antibody linked together by a chain of amino acids.)

When antibodies, including antibody fragments, constitute part or all of the ligands, they preferably are of human origin or are modified to be suitable for use in humans. So-called "humanized antibodies" are well known in the art. See, e.g., Osbourn et al., 2003. They have been modified by genetic manipulation and/or in vitro treatment to reduce their antigenicity in a human. Methods for humanizing antibodies are described, e.g., in U.S. Pat. No. 6,639,055, U.S. Pat. No. 5,585,089, and U.S. Pat. No. 5,530,101. In the simplest case, humanized antibodies are formed by grafting the antigen-binding loops, known as complementarity-determining regions (CDRs), from a mouse mAb into a human IgG. See Jones et al., 1986; Riechmann et al., 1988; Verhoeyen et al., 1988. The generation of high-affinity humanized antibodies, however, generally requires the transfer of one or more additional residues from the so-called framework regions (FRs) of the mouse parent mAb. Several variants of the humanization technology also have been developed. See Vaughan et al., 1998.

Human antibodies, rather than "humanized antibodies," also can be employed in the invention. They have high affinity for their respective antigens and are routinely obtained from very large, single-chain variable fragments (scFvs) or Fab phage display libraries. See Griffiths et al., 1994; Vaughan et al., 1996; Sheets et al., 1998; de Haard et al., 1999; and Knappik et al., 2000.

Useful ligands also include bispecific single chain antibodies, which typically are recombinant polypeptides consisting of a variable light chain portion covalently attached through a linker molecule to a corresponding variable heavy chain portion. See U.S. Pat. No. 5,455,030, U.S. Pat. No. 5,260,203, and U.S. Pat. No. 4,496,778. Bispecific antibodies also can be made by other methods. For example, chemical heteroconjugates can be created by chemically linking intact antibodies or antibody fragments of different specificities. See Karpovsky et al., 1984. However, such heteroconjugates are difficult to make in a reproducible manner and are at least twice as large as normal monoclonal antibodies. Bispecific antibodies also can be created by disulfide exchange, which involves enzymatic cleavage and reassociation of the antibody fragments. See Glennie et al., 1987.

Because Fab and scFv fragments are monovalent they often have low affinity for target structures. Therefore, preferred ligands made from these components are engineered into dimeric, trimeric or tetrameric conjugates to increase functional affinity. See Tomlinson and Holliger, 2000; Carter, 2001; Hudson and Souriau, 2001; and Todorovska et al., 2001. Such conjugate structures can be created by chemical and/or genetic cross-links.

Bispecific ligands of the invention preferably are monospecific at each end, i.e., specific for a single component on minicells at one end and specific for a single component on target cells at the other end. The ligands can be multivalent at one or both ends, for example, in the form of so-called diabodies, triabodies and tetrabodies. See Hudson and Souriau, 2003. A diabody is a bivalent dimer formed by a non-covalent association of two scFvs, which yields two Fv binding sites. Likewise, a triabody results from the formation of a trivalent trimer of three scFvs, yielding three binding sites, and a tetrabody results from the formation of a tetravalent tetramer of four scFvs, yielding four binding sites.

Several humanized, human, and mouse monoclonal antibodies and fragments thereof that have specificity for receptors on mammalian cells have been approved for human therapeutic use, and the list is growing rapidly. See Hudson and Souriau, 2003. An example of such an antibody that can be used to form one arm of a bispecific ligand has specificity for HER2: Herceptin™; Trastuzumab.

Antibody variable regions also can be fused to a broad range of protein domains. Fusion to human immunoglobulin domains such as IgG1 CH3 both adds mass and promotes dimerization. See Hu et al., 1996. Fusion to human Ig hinge-Fc regions can add effector functions. Also, fusion to heterologous protein domains from multimeric proteins promotes multimerization. For example, fusion of a short scFv to short amphipathic helices has been used to produce miniantibodies. See Pack and Pluckthun, 1992. Domains from proteins that form heterodimers, such as fos/jun, can be used to produce bispecific molecules (Kostelny et al., 1992) and, alternately, homodimerization domains can be engineered to form heterodimers by engineering strategies such as "knobs into holes" (Ridgway et al., 1996). Finally, fusion protein partners can be selected that provide both multimerization as well as an additional function, e.g. streptavidin. See Dubel et al., 1995.

Delivery to Phagocytosis- or Endocytosis-Competent Cells

The invention further provides for delivery by means of bringing bacterially derived minicells into contact with mammalian cells that are phagocytosis- or endocytosis-competent. Such mammalian cells, which are capable of engulfing parent bacterial cells in the manner of intracellular bacterial pathogens, likewise engulf the minicells, which release their payload into the cytoplasm of the mammalian cells. This delivery approach can be effected without the use of targeting ligands.

A variety of mechanisms can be involved in the engulfing of minicells by a given type of cell, and the present invention is not dependent on any particular mechanism in this regard. For example, phagocytosis is a well-documented process in which macrophages and other phagocyte cells, such as neutrophils, ingest particles by extending pseudopodia over the particle surface until the particle is totally enveloped. Although described as "non-specific" phagocytosis, the involvement of specific receptors in the process has been demonstrated. See Wright et al., (1986); Speert et al., (1988).

Thus, one form of phagocytosis involves interaction between surface ligands and ligand-receptors located at the membranes of the pseudopodia. This attachment step, mediated by the specific receptors, is thought to be dependent on bacterial surface adhesins. With respect to less virulent bacteria, such as non-enterotoxigenic *E. coli*, phagocytosis also can occur in the absence of surface ligands for phagocyte receptors. See Pikaar et al. (1995), for instance. Thus, the present invention encompasses but is not limited to the use of minicells that either possess or lack surface adhesins, in keeping with the nature of their parent bacterial cells, and are engulfed by phagocytes (i.e., "phagocytosis-competent" host cells), of which neutrophils and macrophages are the primary types in mammals.

Another engulfing process is endocytosis, by which intracellular pathogens exemplified by species of *Salmonella, Escherichia, Shigella, Helicobacter, Pseudomonas* and Lactobacilli gain entry to mammalian epithelial cells and replicate there. Two basic mechanisms in this regard are Clathrin-dependent receptor-mediated endocytosis, also known as "coated pit endocytosis" (Riezman, 1993), and Clathrin-independent endocytosis (Sandvig & Deurs, 1994). Either or both can be involved when an engulfing-competent cell that acts by endocytosis (i.e., an "endocytosis-competent" host cell) engulfs minicells in accordance with the invention. Representative endocytosis-competent cells are breast epithelial cells, enterocytes in the gastrointestinal tract, stomach epithelial cells, lung epithelial cells, and urinary tract and bladder epithelial cells.

When effecting delivery to an engulfing-competent mammalian cell without the use of a targeting ligand, the nature of the application contemplated will influence the choice of bacterial source for the minicells employed. For example, *Salmonella, Escherichia* and *Shigella* species carry adhesins that are recognized by endocytosis-mediating receptors on enterocytes in the gastrointestinal tract, and can be suitable to deliver a drug that is effective for colon cancer cells. Similarly, minicells derived from *Helicobacter pylori*, carrying adhesins specific for stomach epithelial cells, could be suited for delivery aimed at stomach cancer cells. Inhalation or insufflation can be ideal for administering intact minicells derived from a *Pseudomonas* species that carry adhesins recognized by receptors on lung epithelial cells. Minicells derived from Lactobacilli bacteria, which carry adhesins specific for urinary tract and bladder epithelial cells, could be well-suited for intraurethral delivery of a drug to a urinary tract or a bladder cancer.

Formulations

In one aspect, there is provided a composition comprising (a) a plurality of intact minicells, each minicell of the plurality encompassing plasmid-free functional nucleic acid, and (b) a pharmaceutically acceptable carrier therefor.

The formulation optionally comprises a drug. In one example, the minicell of the formulation contains the drug, while in another the minicell can contain a nucleic acid molecule, such as a plasmid, that encodes the drug.

The formulations also optionally contain a bispecific ligand for targeting the minicell to a target cell. The minicell and ligand can be any of those described herein. Thus, the minicell contains a nucleic acid encoding a functional nucleic acid and the bispecific ligand preferably is capable of binding to a surface component of the minicell and to a surface component of a target mammalian cell.

Formulations can be presented in unit dosage form, e.g., in ampules or vials, or in multi-dose containers, with or without an added preservative. The formulation can be a solution, a suspension, or an emulsion in oily or aqueous vehicles, and can contain formulatory agents, such as suspending, stabilizing and/or dispersing agents. A suitable solution is isotonic with the blood of the recipient and is illustrated by saline, Ringer's solution, and dextrose solution. Alternatively, formulations can be in lyophilized powder form, for reconstitution with a suitable vehicle, e.g., sterile, pyrogen-free water or physiological saline. The formulations also can be in the form of a depot preparation. Such long-acting formulations can be administered by implantation (for example, subcutaneously or intramuscularly) or by intramuscular injection.

Administration Routes

Formulations described herein can be administered via various routes and to various sites in a mammalian body, to achieve the therapeutic effect(s) desired, either locally or systemically. Delivery can be accomplished, for example, by oral administration, by application of the formulation to a body cavity, by inhalation or insufflation, or by parenteral, intramuscular, intravenous, intraportal, intrahepatic, peritoneal, subcutaneous, intratumoral, or intradermal administration. The mode and site of administration is dependent on the location of the target cells. For example, cystic-fibrotic cells can be efficiently targeted by inhaled delivery of the targeted minicells. Similarly, tumor metastasis can be more efficiently treated via intravenous delivery of targeted minicells. Primary ovarian cancer can be treated via intraperitoneal delivery of targeted minicells.

Purity

In one aspect, minicells are substantially free from contaminating parent bacterial cells. Thus, minicell-containing formulations preferably contain fewer than about 1 contaminating parent bacterial cell per $10^7$ minicells, more preferably contain fewer than about 1 contaminating parent bacterial cell per $10^8$ minicells, even more preferably contain fewer than about 1 contaminating parent bacterial cell per $10^9$ minicells, still more preferably contain fewer than about 1 contaminating parent bacterial cell per $10^{10}$ minicells and most preferably contain fewer than about 1 contaminating parent bacterial cell per $10^{11}$ minicells.

Methods of purifying minicells are known in the art and described in international publication number WO03/033519. One such method combines cross-flow filtration (feed flow is parallel to a membrane surface; Forbes, 1987) and dead-end filtration (feed flow is perpendicular to the membrane surface). Optionally, the filtration combination can be preceded by a differential centrifugation, at low centrifugal force, to remove some portion of the bacterial cells and thereby enrich the supernatant for minicells.

Another purification method employs density gradient centrifugation in a biologically compatible medium. After centrifugation, a minicell band is collected from the gradient, and, optionally, the minicells are subjected to further rounds of density gradient centrifugation to maximize purity. The method can further include a preliminary step of performing differential centrifugation on the minicell-containing sample. When performed at low centrifugal force, differential centrifugation will remove some portion of parent bacterial cells, thereby enriching the supernatant for minicells.

Particularly effective purification methods exploit bacterial filamentation to increase minicell purity. Thus a minicell purification method can include the steps of (a) subjecting a sample containing minicells to a condition that induces parent bacterial cells to adopt a filamentous form, followed by (b) filtering the sample to obtain a purified minicell preparation.

Known minicell purification methods also can be combined. One highly effective combination of methods is as follows:

Step A: Differential centrifugation of a minicell producing bacterial cell culture. This step, which can be performed at 2000 g for about 20 minutes, removes most parent bacterial cells, while leaving minicells in the supernatant.

Step B: Density gradient centrifugation using an isotonic and non-toxic density gradient medium. This step separates minicells from many contaminants, including parent bacterial cells, with minimal loss of minicells. Preferably, this step is repeated within a purification method.

Step C: Cross-flow filtration through a 0.45 μm filter to further reduce parent bacterial cell contamination.

Step D: Stress-induced filamentation of residual parent bacterial cells. This can be accomplished by subjecting the minicell suspension to any of several stress-inducing environmental conditions.

Step E: Antibiotic treatment to kill parent bacterial cells.

Step F: Cross-flow filtration to remove small contaminants, such as membrane blebs, membrane fragments, bacterial debris, nucleic acids, media components and so forth, and to concentrate the minicells. A 0.2 μm filter can be employed to separate minicells from small contaminants, and a 0.1 μm filter can be employed to concentrate minicells.

Step G: Dead-end filtration to eliminate filamentous dead bacterial cells. A 0.45 um filter can be employed for this step.

Step H: Removal of endotoxin from the minicell preparation. Anti-Lipid A coated magnetic beads can be employed for this step.

Administration Schedules

In general, the formulations disclosed herein can be used at appropriate dosages defined by routine testing, to obtain optimal physiological effect, while minimizing any potential toxicity. The dosage regimen can be selected in accordance with a variety of factors including age, weight, sex, medical condition of the patient; the severity of the condition to be treated, the route of administration, and the renal and hepatic function of the patient.

Optimal precision in achieving concentrations of minicell and drug within the range that yields maximum efficacy with minimal side effects can require a regimen based on the kinetics of the functional nucleic acid and drug availability to target sites and target cells. Distribution, equilibrium, and elimination of a minicell or drug can be considered when determining the optimal concentration for a treatment regimen. The dosages of the minicells and drugs can be adjusted when used in combination, to achieve desired effects.

Moreover, the dosage administration of the formulations can be optimized using a pharmacokinetic/pharmacodynamic modeling system. For example, one or more dosage regimens can be chosen and a pharmacokinetic/pharmacodynamic model can be used to determine the pharmacokinetic/pharmacodynamic profile of one or more dosage regimens. Next, one of the dosage regimens for administration can be selected which achieves the desired pharmacokinetic/pharmacodynamic response based on the particular pharmacokinetic/pharmacodynamic profile. See, e.g., WO 00/67776. In this regard, a dosage regimen for any indication can be determined using the approach and model described herein at Example 6, modified for the particular cell of interest.

Specifically, the formulations can be administered at least once a week over the course of several weeks. In one embodiment, the formulations are administered at least once a week over several weeks to several months.

More specifically, the formulations can be administered at least once a day for about 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days. Alternatively, the formulations can be administered about once every day, about once every 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days or more.

The formulations can alternatively be administered about once every week, about once every 2, 3, 4, 5, 6, 7, 8, 9, 10, 11, 12, 13, 14, 15, 16, 17, 18, 19 or 20 weeks or more. Alternatively, the formulations can be administered at least once a week for about 2, 3, 4, 5, 6, 7, 8, 9, 10, 11, 12, 13, 14, 15, 16, 17, 18, 19 or 20 weeks or more.

Alternatively, the formulations can be administered about once every month, about once every 2, 3, 4, 5, 6, 7, 8, 9, 10, 11 or 12 months or more.

The formulations can be administered in a single daily dose, or the total daily dosage can be administered in divided doses of two, three, or four times daily.

In method in which minicells are administered before a drug, administration of the drug can occur anytime from several minutes to several hours after administration of the minicells. The drug can alternatively be administered anytime from several hours to several days, possibly several weeks up to several months after the minicells.

More specifically, the functional nucleic acid-packaged minicells can be administered at least about 1, 2, 3, 4, 5, 6, 7, 8, 9, 10, 11, 12, 13, 14, 15, 16, 17, 18, 19, 20, 21, 22, 23 or 24 hours before the drug. Moreover, the minicells can be administered at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days before the administration of the drug. In yet another embodiment, the minicells can be administered at least about 1, 2, 3, 4, 5, 6, 7, 8, 9, 10, 11, 12, 13, 14, 15, 16, 17, 18, 19 or 20 weeks or more before the drug. In a further embodiment, the minicells can be administered at least about 1, 2, 3, 4, 5, 6, 7, 8, 9, 10, 11 or 12 months before the drug.

In another embodiment, the minicell is administered after the drug. The administration of the minicell can occur anytime from several minutes to several hours after the administration of the drug. The minicell can alternatively be administered anytime from several hours to several days, possibly several weeks up to several months after the drug.

The following examples are illustrative only, rather than limiting, and provide a more complete understanding of the invention.

EXAMPLES

1. Direct Packaging of Regulatory RNA into Intact Minicells In Vitro

Bacterially derived intact minicells were prepared and purified as described in U.S. Published Application No. US 2004/0265994. Cy3-labeled glyceraldehydes-3-phosphate dehydrogenase (GAPDH) siRNA was obtained (excitation max ($\lambda_{max}$) 547 nm, emission max ($\lambda_{max}$) 563 nm), product of Ambion (Austin, Tex. USA), and was reconstituted in nuclease-free water to a final concentration of 50 µM.

Approximately $10^7$ minicells were resuspended in 1× Phosphate Buffer Solution (PBS) (Gibco) and were co-incubated with 1 µM of Cy3-labeled GAPDH siRNA. The incubation was carried out for 2 hours at 37° C., with gentle mixing. Control minicells were mock loaded by incubation with 1×PBS alone. Post loading minicells were pelleted and washed twice with 1×PBS by centrifugation for 10 minutes at 16,200×g. Experimental and control minicells were observed under a fluorescence DMLB microscope, product of Leica (Germany) with attached D70 camera, product of Olympus Microscopes (Germany). Images were acquired using 100× oil immersion lens.

The above co-incubation experiments were also carried out under different experimental conditions such as incubation at room temperature, 37° C., and 4° C. Additionally, the co-incubation times were varied to include 1 hour, 2 hours, 4 hours, and 12 hours, respectively.

Figure 1B:
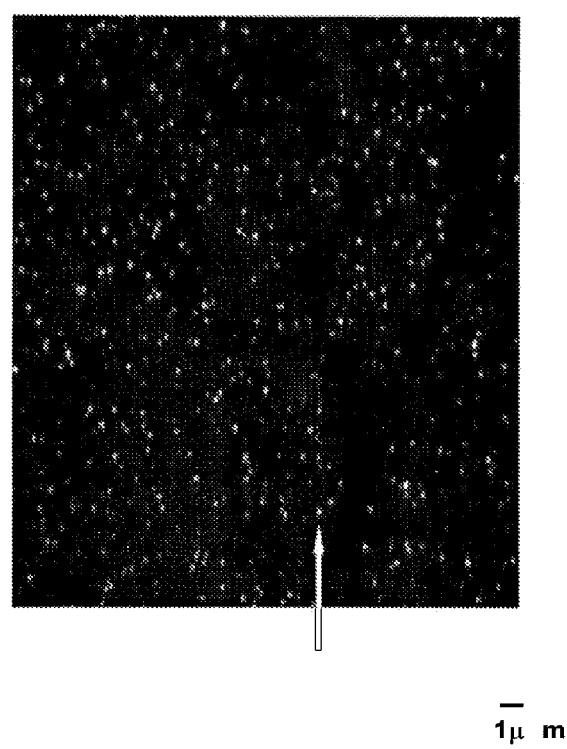

As shown in FIG. 1B, the intact the siRNA molecules rapidly diffused into the minicells. The 2-hour incubation at 37° C. was sufficient to achieve highly significant packaging of the minicells.

In order to determine whether the siRNA molecules were inside the minicells or adherent on minicell surfaces, the minicells with Cy3-fluorescence-labeled siRNA were incubated with exonucleases overnight, followed by a repeat of fluorescence microscopy. The results were identical to those shown in FIG. 1B, indicating that the siRNAs were internalized by the minicells and were not adherent on the minicell surface.

2. In Vitro Transfection of Human Breast Cancer Cells with Regulatory RNA-Packaged, Bispecific Antibody-Targeted Minicells To demonstrate that minicells carrying regulatory RNA are stable in serum in-vitro and that they can be internalized by specifically-targeted mammalian cells, the following experiment was carried out.

siRNA directed to polo-kinase 1 (Plk1) was synthesized with a target sequence 5'-GGTGGATGTGTGGTC-CATTTT-3', and tagged with a fluorescent tag, AlexaFluor 488. Polio kinases have multiple functions during the entry into mitosis, centrosome maturation, bipolar spindle formation, the segregation of chromosomes and cytokinesis, and, crucially, the fidelity monitoring of checkpoint control (Glover et al., 1998; Barr et al., 2004; van de Weerdt and Medema 2006). In humans, Plk1 is the best characterized member of this family. Plk1 is associated with tumorigenesis and belongs to the family of serine/threonine kinases, which represent attractive targets for novel chemotherapeutics. Accordingly, Plk1 is deemed a promising target for anticancer drug development (Strebhardt and Ullrich, 2006).

Minicells were purified, and $10^9$ minicells were packaged with anti-$^{AF488}$Plk1 siRNA, as described in Example 1. A bispecific antibody (BsAb) was prepared, carrying anti-*S. typhimurium* O-antigen and anti-human EGFR specificities, and was attached to the minicells$_{AF488\text{-}Plk1\text{-}siRNA}$ as described in PCT published application WO 05/056749. The resultant minicells were designated $^{EGFR}$minicells$_{AF488\text{-}Plk1\text{-}siRNA}$. These minicells ($10^9$) were incubated with human breast cancer cells, in tissue culture, at a density of 10,000 minicells:1 tumor cell. The incubation was carried out for 1 hour, 2 hours, 4 hours and 24 hours. At each time point, the cells were collected and stained with DAPI (nuclear stain, blue fluorescence). The cells were observed using the IX81 confocal microscope (Olympus) and the CellR software.

Figure 2:
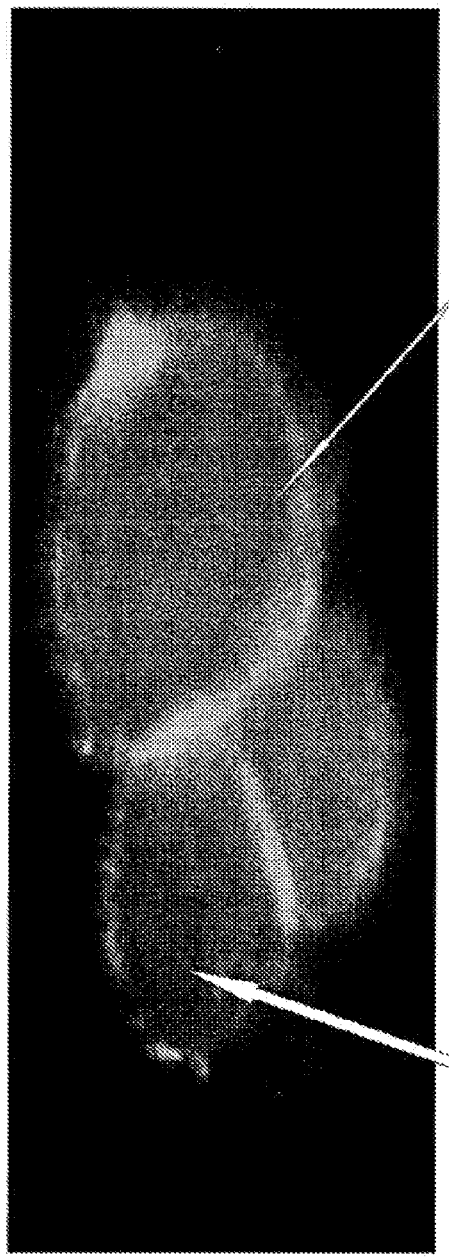
FIG. 2 is an image captured by fluorescence confocal microscopy and shows the adhesion and internalization of EGFR-targeted, siRNA-Plk1-packaged minicells into human breast cancer cells in-vitro.

By 1 hour the fluorescent, siRNA-carrying minicells had adhered to the MDA-MB-468 cells (see FIG. 2). This attachment was due, it is believed, to the binding to the minicell-attached BsAb, which targeted the EGF receptor on the MDA-MB-468 cells, since the control incubation with non-targeted minicells$_{AF488\text{-}Plk1\text{-}siRNA}$ were washed away and did not show any green fluorescence associated with the MDA-MB-468 cells. By 2 hours post-incubation EGFR, the minicells$_{AF488\text{-}Plk1\text{-}siRNA}$ were internalized within the MDA-MB-468 cells and exhibited intense green fluorescence. By 24 hours most of the green fluorescence was gone, indicating that the internalized minicells had been broken down, presumably within the phagolysosomes.

3. Extraction and Quantification of siRNA from Intact Minicells

Since siRNAs do not occur naturally in bacterial cells or bacterially-derived minicells, it is unsurprising that no established methodology exists for extracting siRNA from such particles. Accordingly, the present inventors developed a method for quantitative extraction of siRNAs that are packaged in intact minicells, pursuant to the invention.

Kinesin spindle protein (KSP), also known as "kinesin-5" and "Eg5," is a microtubule motor protein. It is essential to the formation of bipolar spindles and to proper segregation of sister chromatids during mitosis (Enos and Morris, 1990; Blangy et al., 1995; Sawin and Mitchison, 1995; Dagenbach and Endow, 2004). Inhibition of KSP causes the formation of monopolar mitotic spindles, activates the spindle assembly checkpoint, and arrests cells at mitosis, leading to subsequent cell death (Blangy et al., 1995, Caner et al., 1999; Kapoor et al., 2000; Tao et al., 2005).

An siRNA against KSP was selected for packaging in minicells, to inform the optimization of siRNA extraction from minicells in accordance with the invention. More specifically, KSP-1-siRNA double-stranded oligonucleotide sequences (sense strand; 5'-AAC TGG ATC GTA AGA AGG CAG-3') were synthesized and packaged into minicells, pursuant to the procedures set out in Example 1, supra.

Minicells$_{siRNA\text{-}KSP}$ ($10^{10}$) and a comparable number of control empty minicells were processed, using a number of commercially available nucleic acid extraction kits. The results showed that the mirVana miRNA isolation kit (Ambion) provided quantitative extraction of the siRNA-KSP from intact minicells. The procedure was carried out according to the manufacturer's instructions.

The purified siRNA first was stained with an ultrasensitive fluorescent nucleic acid dye, RiboGreen™, product of Molecular Probes Inc. (Eugene, Oreg. USA), followed by quantitation using the NanoDrop ND-3300 Fluorospectrometer, product of NanoDrop Technologies Inc. (Wilmington, Del. USA), also according to the manufacturer's instructions. RNA-bound RiboGreen™ has an excitation maximum of ~500 nm and an emission maximum of ~525 nm.

The results showed that the minicells were able to carry the siRNAs. $10^{10}$ empty minicells carried ~1.4 µg RNA, presumably a background level of endogenously formed bacterial RNA. The same number of minicells$_{siRNA\text{-}KSP}$ carried ~2.7 µg RNA, comprising endogenous bacterial RNA plus exogenously packaged siRNA-KSP Thus, these data demonstrate that $10^{10}$ minicells can package at least ~1.3 µg of exogenously packaged siRNA.

4. In Vivo Demonstration of Anti-Tumor Effects Achieved by Regulatory RNA-Packaged Minicells The following studies were conducted to show that regulatory RNA-packaged minicells could deliver intact, regulatory RNA in therapeutically effective concentrations to tumor cells in vivo.

siRNA against KSP, as described in Examiner 3, was selected to package in the minicells according to the present invention. Minicells were purified, and $10^9$ minicells were packaged with anti-KSP siRNA, as described in Example 1. A BsAb also was prepared and attached to the minicells$_{siRNA-KSP}$, as described in Example 2, to generate $^{EGFR}$minicells$_{siRNA-KSP}$.

The mice used in this example were purchased from Animal Resources Centre (Perth, Wash., Australia), and all animal experiments were performed in compliance with the guide of care and use of laboratory animals, with Animal Ethics Committee approval. The experiments were performed in the NSW Agriculture-accredited small animal facility at EnGeneIC Pty Ltd (Sydney, New South Wales, Australia).

Human breast cancer cells (MDA-MB-468, ATCC) were grown in tissue culture in RPMI 1640 medium supplemented with GIBCO-BRL 5% Bovine Calf Serum, product of Invitrogen Corporation (Carlsbad, Calif. USA), and glutamine (Invitrogen) in a humidified atmosphere of 95% air and 5% $CO_2$ at 37° C. $1 \times 10^6$ cells in 50 µl serum-free media were mixed together with 50 µl growth factor reduced matrigel, product of BD Biosciences (Franklin Lakes, N.J. USA). By means of a 23-gauge needle, the cells were injected subcutaneously between the shoulder blades of each mouse. The tumors were measured twice a week, using an electronic digital caliper (precision to 0.001), product of Mitutoyo (Japan), and mean tumor volume was calculated using the formula: length (mm)×width$^2$ (mm)×0.5=volume (mm$^3$).

The various treatments commenced once the tumors reached volumes between 170 mm$^3$ and 200 mm$^3$, and mice were randomized to two different groups of eight per group. Control group 1 received sterile saline, while experimental group 2 received $^{EGFR}$minicells$_{siRNA-KSP}$. ($10^9$), four times per week.

Figure 3:
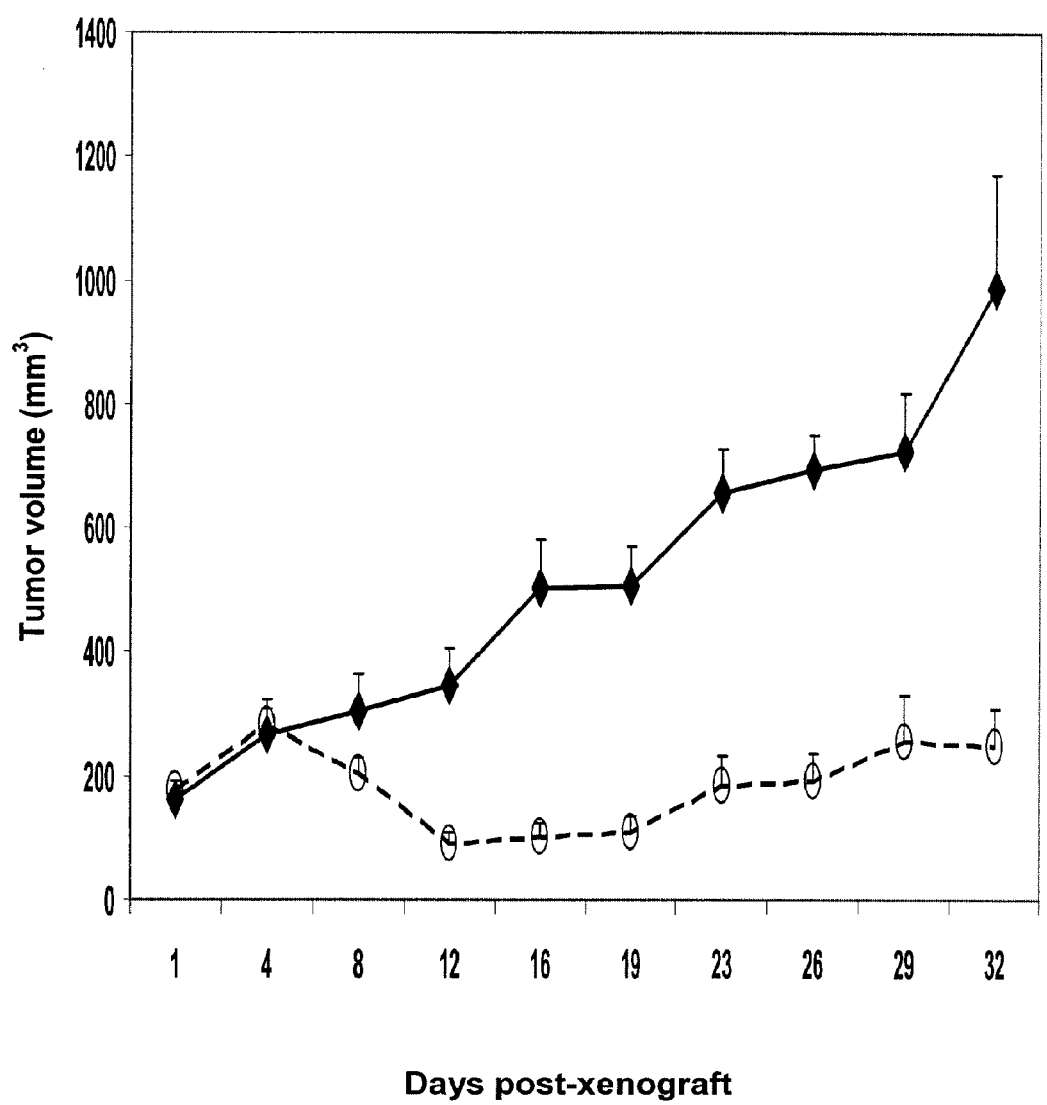
FIG. 3 graphically shows a significant anti-tumor effect achieved by treating human breast cancer (MDA-MB-468) xenografts in nude mice with EGFR-targeted, KSP-siRNA-packaged minicells. Control group 1(◆) received sterile saline, while experimental group 2 (⊖) received $^{EGFR}$minicells$_{siRNA-KSP}$ ($10^9$), four times per week.

As shown in FIG. 3, $^{EGFR}$minicells$_{siRNA-KSP}$ provided a highly significant anti-tumor effect compared to the saline controls. The results demonstrate that (a) siRNAs were stable within the minicells in vivo, (b) intact and fully functional siRNAs were delivered to the tumor cells in vivo, and (c) the minicell delivered therapeutically significant concentrations of siRNA to the tumor cells in vivo.

5. Demonstration of Tailor-Made Cancer Therapy Via Treatment with Regulatory RNA-Packaged Minicells, Followed by Drug-Packaged Minicells Most anti-cancer therapies are associated with drug resistance. The same is true for regulatory RNA treatments, since genetic mutations in tumor cells can render the regulatory RNA ineffective if the target gene mutates within the sequence targeted by the regulatory RNA.

There has been no effective strategy to address drug resistance in cancer patients. Instead, new drugs must be administered to bypass the mutation. This approach faces serious difficulties, however, since most anti-cancer drugs are highly toxic, and combined therapies augment that toxicity, resulting in dose limitation and frequent abandonment of therapy when the patient can no longer cope with the toxicity. The following study was conducted to assess the efficacy of regulatory RNA-packaged minicells in addressing such resistance.

As described above, minicells were purified and packaged ($10^9$) with anti-KSP or anti-Plk1 siRNA. Also as previously described, bispecific antibody was prepared, carrying anti-*S. typhimurium* O-antigen and anti-human EGFR specificities, and was attached to the minicells$_{siRNA-KSP}$ to generate $^{EGFR}$minicells$_{siRNA-KSP}$.

Human colon cancer (HCT116; ATCC) xenografts were established in nude mice, as described in Example 3, and were treated i.v. as follows: Group 1 mice received sterile saline, and mice of groups 2, 3 and 4 were treated for the first 10 doses (see FIG. 4) with $10^9$ $^{EGFR}$minicells$_{siRNA-Plk1}$, $^{EGFR}$minicells$_{siRNA-KSP-1}$, and $^{EGFR}$minicells$_{siRNA-KSP-2}$, respectively. The Plk1 and KSP-1 sequences were as shown in the examples above. siRNA-KSP-2 (sense strand; 5' CTGAAGACC TGAAGACAAT 3') targets a different segment of KSP mRNA. After day 33, mice in groups 2, 3 and 4 were treated with two doses of $^{EGFR}$minicells$_{carboplatin}$.

Figure 4:
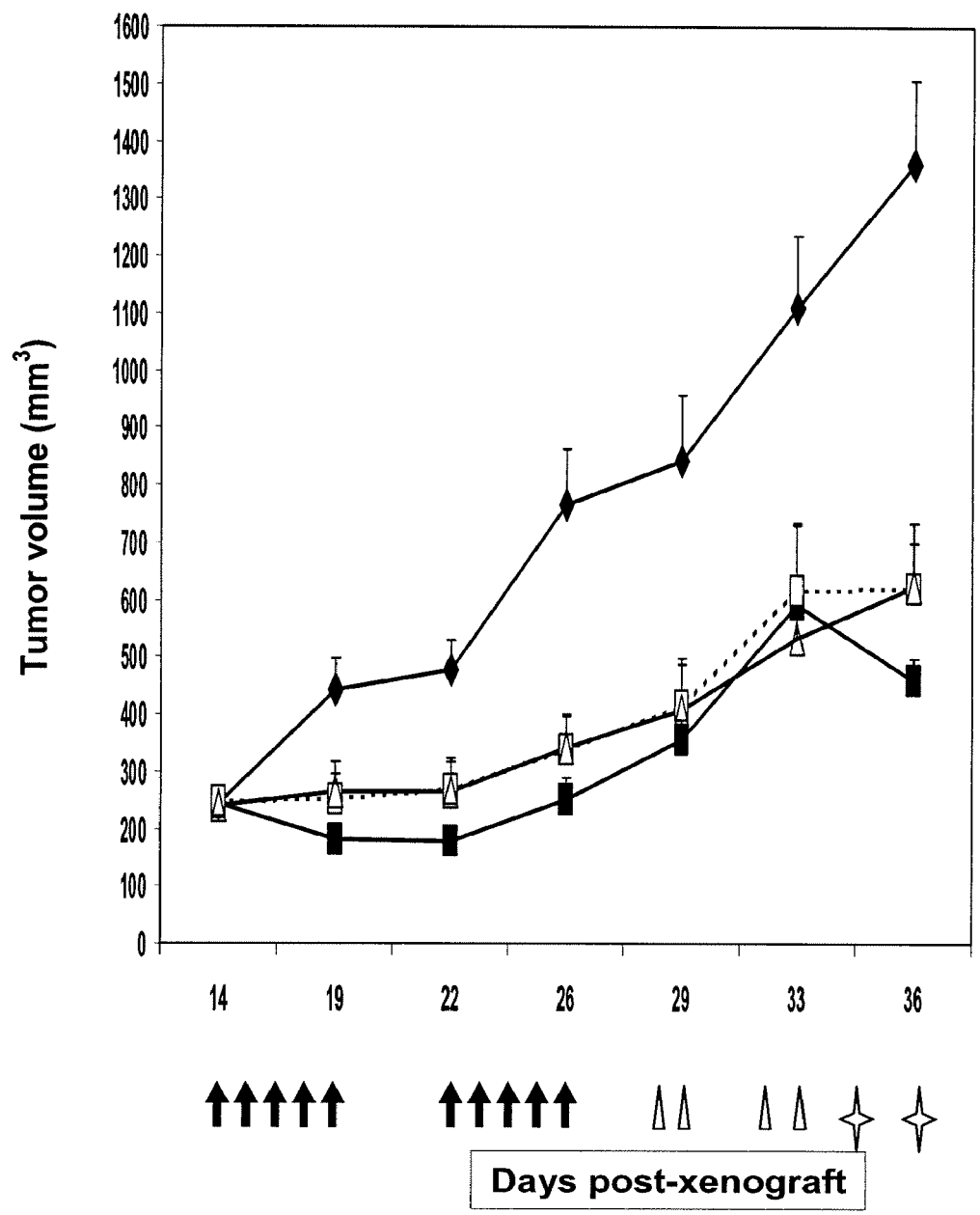
FIG. 4 graphically depicts a significant anti-tumor effect achieved by treating human colon cancer (HCT116) xenografts in nude mice with EGFR-targeted, KSP-siRNA-packaged minicells in conjunction with EGFR-targeted, carboplatin-packaged minicells. Group 1 (◆) mice received sterile saline, and mice of groups 2 (▲), 3 (■) and 4 (□) were treated for the first 10 doses (see FIG. 4) with $10^9$ $^{EGFR}$minicells$_{siRNA-Plk1}$, $^{EGFR}$minicells$_{siRNA-KSP-1}$, and $^{EGFR}$minicells$_{siRNA-KSP-2}$, respectively.

The results showed (FIG. 4) that post-day 26, the tumors were becoming resistant to the siRNA treatments. Accordingly, the mice in groups 2, 3 and 4 were treated for the four subsequent doses, with all three doses $^{EGFR}$minicells$_{siRNA-Plk1}$, +$^{EGFR}$minicells$_{siRNA-KSP-1}$, +$^{EGFR}$minicells$_{siRNA-KSP-2}$) combined in equal quantities, i.e., ~3×10 of each minicell type. In addition, by day 33 the tumors were highly resistant to all the siRNAs (FIG. 4). Following administration of $^{EGFR}$minicells$_{carboplatin}$, the tumor growth in groups 3 and 4 mice was retarded significantly. Following administration of $^{EGFR}$minicells$_{carboplatin}$, group 3 mice showed a significant regression in tumor volume.

These data show that drug-resistant tumor cells can be treated effectively in vivo, pursuant to the present invention. In particular, (1) sequential administrations of targeted minicells, carrying regulatory RNA sequences designed to reduce tumor burden significantly, are followed, when the tumor cells become resistant to the siRNA-mediated antitumor effect, by (2) targeted minicells carrying a drug that does not act on the same protein targeted by the regulatory RNA.

6. Demonstration of Target Protein Knockdown in Tumor Cells and Resultant Arrest in Cell Growth Following Targeted Delivery of a Therapeutically Effective Amount of Regulatory RNA Packaged in Intact Minicells To demonstrate that the inventive methods package therapeutically effective amounts of regulatory RNA in intact minicells, it was necessary to demonstrate that bispecific antibody-targeted, regulatory RNA-packaged minicells could efficiently and effectively trigger tumor cell-growth arrest and induce apoptotic cell death.

In a humidified atmosphere of 95% air and 5% $CO_2$ at 37° C., human colonic epithelial cancer cells (HCT116) were grown in tissue culture in RPMI 1640 medium, supplemented with 5% Bovine Calf Serum and glutamine. As described above, minicells were purified, were packaged with siRNA directed against Plk1 or KSP, and were attached to a BsAb that carried anti-*S. typhimurium* O-antigen and anti-human EGFR specificities. Thus, from the minicells$_{siRNA-KSP}$, minicells$_{siRNA-Plk1}$, and minicells (control) were generated $^{EGFR}$minicells$_{siRNA-KSP}$, $^{EGFR}$minicells$_{siRNA-Plk1}$ and $^{EGFR}$minicells. HCT116 cells were seeded in six-well plates, and the experimental and control groups were transfected at a ratio of 5,000 minicells: 1 HCT116 cell. An additional, cells-only control was included.

After 2 hours incubation with minicells, the wells were washed three times with fresh PBS. Wells were harvested at 4 hours, 8 hours, 16 hours, 24 hours, 32 hours and 48 hours post-transfection, and cells were fixed in cold 70% ethanol and incubated at 4° C. for 30 minutes. The cells were washed twice in phosphate-citrate buffer (pH 7.8) and were treated with 100 mg/ml of RNAse, to ensure that only the DNA was stained. The cells were stained with propidium iodide (nucleic acid stain) and then were analyzed using a FACSCalibur™ flow cytometer, product of Becton Dickinson (Franklin Lakes, N.J. USA), at Macquarie University (Sydney, Australia), and the CELL Quest acquisition-and-analysis software, also a Becton Dickinson product.

Figures 5A, 5B, 5C, 5D, 5E, 5F, 5G, 5H:
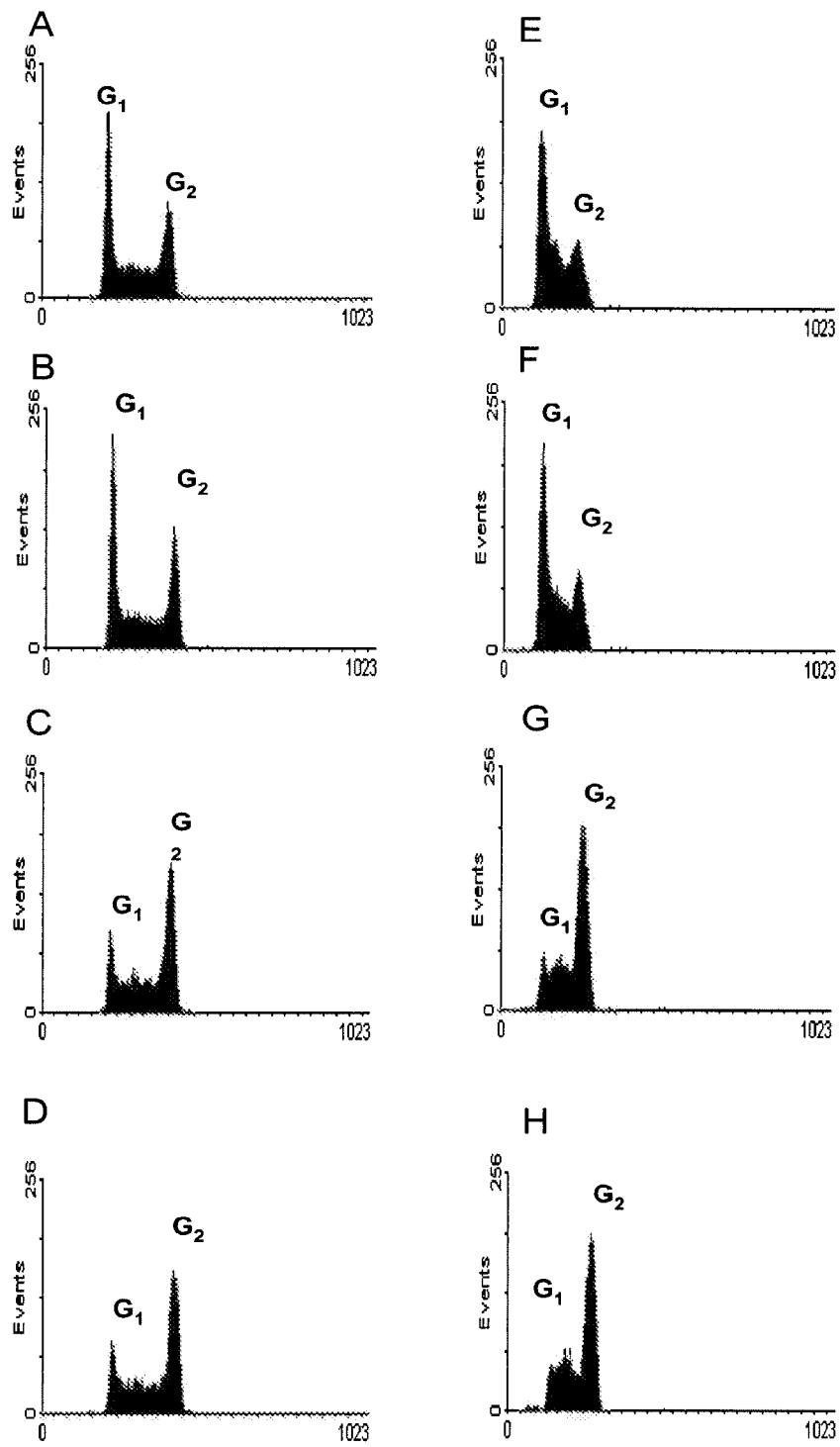
FIGS. 5A-5H provides FACS analysis, from various times post-transfection, of colon cancer (HCT116) cells treated with experimental minicells, $^{EGFR}$minicells$_{siRNA-KSP}$ or $^{EGFR}$minicells$_{siRNA-Plk1}$.
Figure 6A:
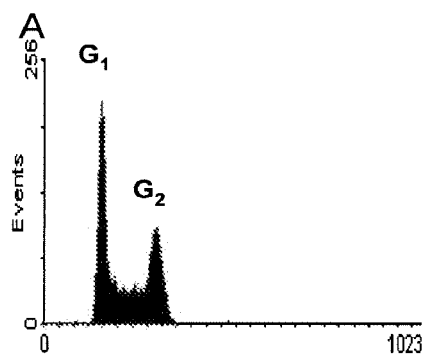
FIGS. 6A-6H provides FACS analysis, from various times post-transfection, of colon cancer (HCT116) cells treated with experimental minicells, $^{EGFR}$minicells$_{siRNA-KSP}$, or $^{EGFR}$minicells$_{siRNA-Plk1}$.
Figure 6B:
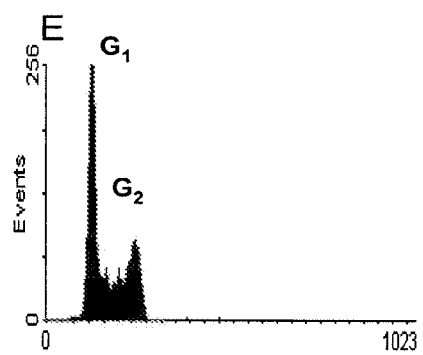
Figure 6C:
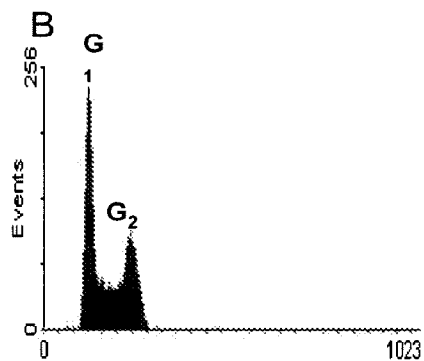
Figure 6D:
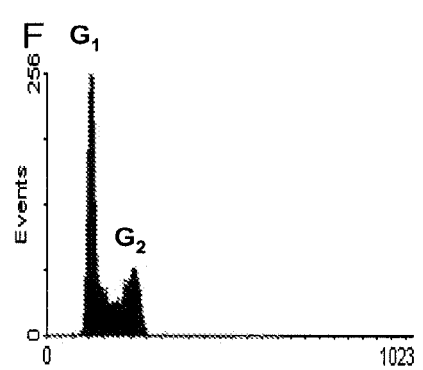
Figure 6E:
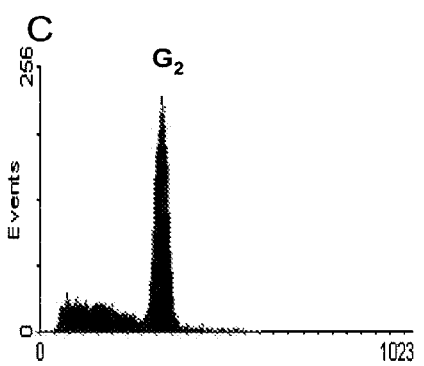
Figure 6F:
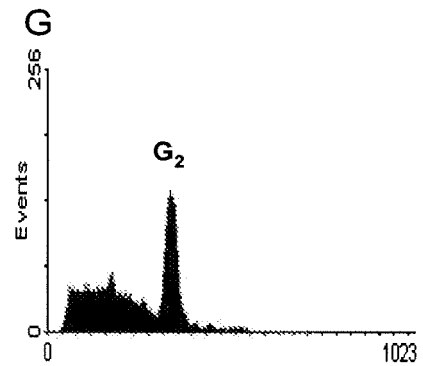
Figure 6G:
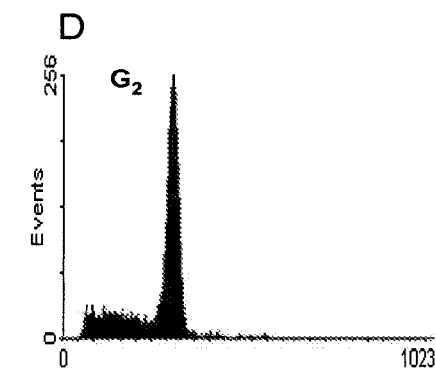
Figure 6H:
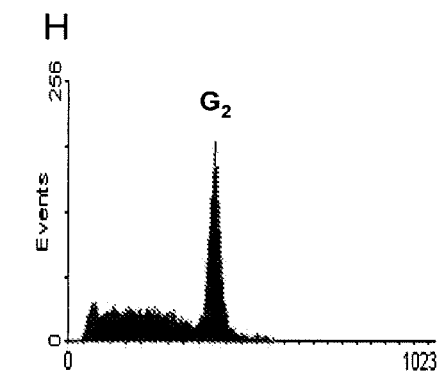
Figures 7A, 7B, 7C, 7D, 7E, 7F, 7G, 7H:
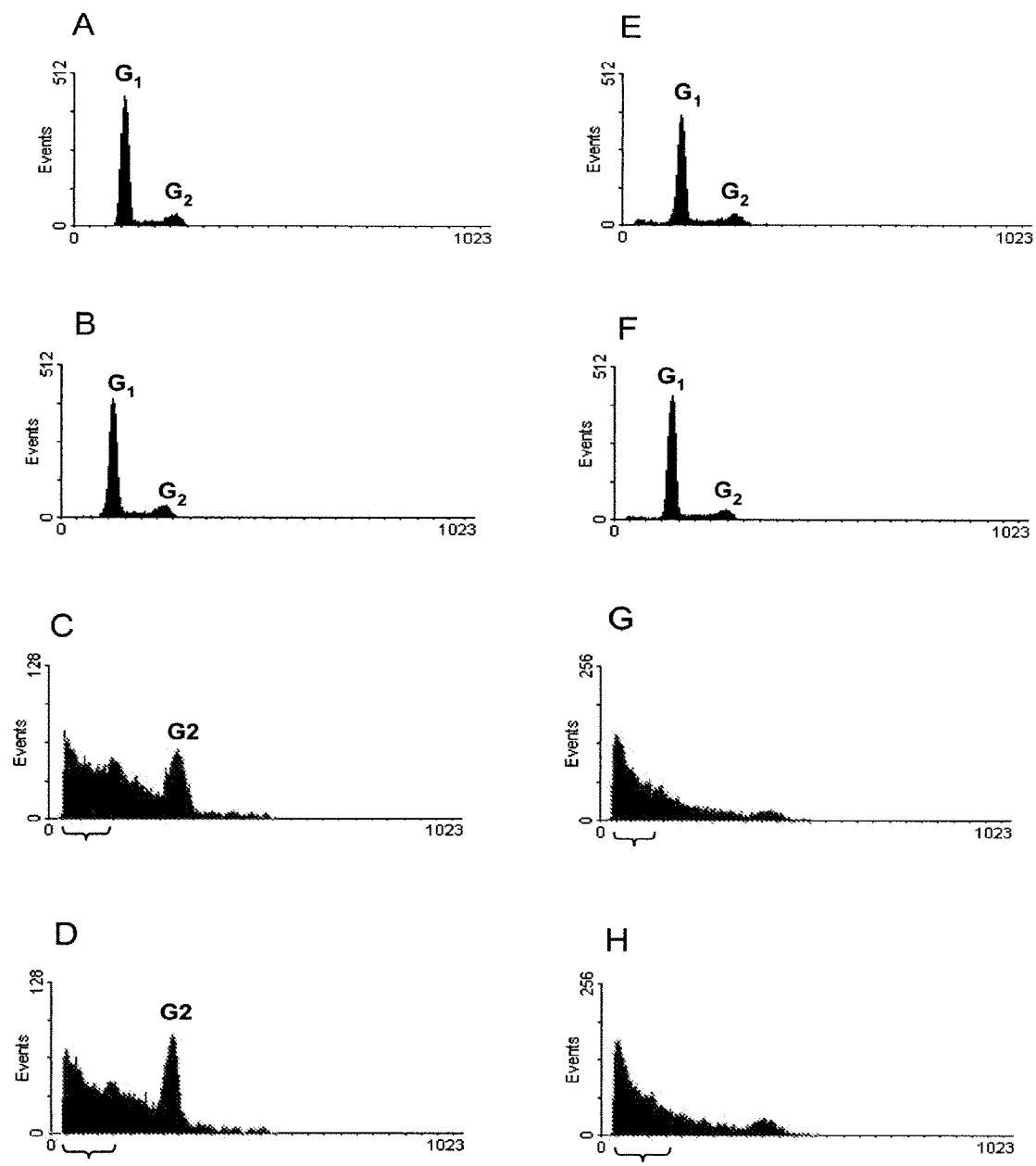
FIGS. 7A-7H provides FACS analysis, from various times post-transfection, of colon cancer (HCT116) cells treated with experimental minicells, $^{EGFR}$minicells$_{siRNA-KSP}$, or $^{EGFR}$minicells$_{siRNA-Plk1}$.

FACS analysis of the cells showed that, by 4 and 8 hours post-transfection (FIG. 5A), cells treated with either $^{EGFR}$minicells$_{siRNA-KSP}$ or $^{EGFR}$minicells$_{siRNA-Plk1}$ were characterized by a robust G2 cell-cycle arrest. Control cells, either cells only or treated with $^{EGFR}$minicells, showed no adverse effects. These cells showed normal G1, S, and G2 phases of the cell cycle. By 16 and 24 hours, the experimental cells displayed not only a robust G2 arrest but also a large number of apoptotic cells (FIG. 6). By 32 and 48 hours, most of the cells in the experimental groups were apoptotic and had turned into cell debris (See in particular brackets in FIG. 7).

These results demonstrate that the targeted intact minicells were packaged with a therapeutically effective amount of regulatory RNA, and that the minicells of the invention were highly efficient and significantly effective in target protein knockdown within tumor cells, resulting in apoptotic cell death.

CITED PUBLICATIONS

Barr, F. A., Sillje, H. H., and Nigg, E. A. Pololike kinases and the orchestration of cell division. *Nat. Rev. Mol. Cell. Biol.* 5: 429-440 (2004).

Batra, R. K., Wang-Johanning, F., Wagner, E., Garver, R. I. Jr., Curiel, D. T. Receptor-mediated gene delivery employing lectin-binding specificity. *Gene Ther.* 1: 255-260 (1994).

Becker, C. M., Farnebo, F. A., Iordanescu, I., Behonick, D. J., Shih, M. C., Dunning, P., Christofferson, R., Mulligan, R. C., Taylor, G. A., Kuo, C. J., Zetter, B. R. Gene therapy of prostate cancer with the soluble vascular endothelial growth factor receptor Flk1. *Cancer Biol. Ther.* 1: 548-553 (2002).

Bertrand, J-R., Pottier, M., Vekris, A., Opolon, P., Maksimenko, A., Malvy, C. Comparison of antisense oligonucleotides and siRNAs in cell culture and in vivo. *Biochem. Biophys. Res. Commun.* 296: 1000-1004 (2002).

Blangy, A., Lane, H. A., d'Herin, P., Harper, M., Kress, M., Nigg, E. A. Phosphorylation by p34cdc2 regulates spindle association of human Eg5, a kinesin-related motor essential for bipolar spindle formation in vivo. *Cell* 83: 1159-1169 (1995).

Borst, P. and Elferink, R. O. Mammalian ABC transporters in health and disease. *Annu. Rev. Biochem.* 71: 537-592 (2002).

Bredel, M. Anticancer drug resistance in primary human brain tumors. *Brain Res. Rev.* 35: 161-204 (2001).

Britton, R. A., Lin, D. C., Grossman, A. D. Characterization of a prokaryotic SMC protein involved in chromosome partitioning. *Genes Dev.* 12: 1254-1259 (1998).

Caplen, N. J. RNAi as a gene therapy approach. *Expert Opin. Biol. Ther.* 3: 575-586 (2003).

Carter, P. Improving the efficacy of antibody-based cancer therapies. *Nat. Rev. Cancer* 1: 118-129 (2001).

Check, E. Gene therapy put on hold as third child develops cancer. *Nature,* 433: 561 (2005).

Chen, Z. S. et al. Reversal of drug resistance mediated by multidrug resistance protein (MRP) 1 by dual effects of agosterol A on MRP1 function. *Int. J. Cancer* 93: 107-113 (2001).

Chiu, Y-L., Rana, T. M. siRNA function in RNAi: a chemical modification analysis. *RNA* 9: 1034-1048 (2003).

Choung, S., Kim, Y. J., Kim, S., Park, H. O., Choi, Y. C. Chemical modification of siRNAs to improve serum stability without loss of efficacy. *Biochem. Biophys. Res. Commun.* 342: 919-927 (2006).

Conner, S. D. and Schmid, S. L. Regulated portals of entry into the cell. *Nature* 422: 37-44 (2003).

Czauderna, F., Fechtner, M., Dames, S., Aygun, H., Klippel, A., Pronk, G. J., Giese, K., Kaufmann, J. Structural variations and stabilising modifications of synthetic siRNAs in mammalian cells. *Nucleic Acids Res.* 31: 2705-2716 (2003).

Dagenbach, E. M., and Endow, S. A. A new kinesin tree. *J. Cell Sci.* 117: 3-7 (2004).

Dash, P. R., Read, M. L., Barrett, L. B., Wolfert, M. A. Seymour, L. W. Factors affecting blood clearance and in vivo distribution of polyelectrolyte complexes for gene delivery. *Gene. Ther.* 6: 643-650 (1999).

de Boer, P. A., Crossley, R. E., Rothfield, L. I. Roles of MinC and MinD in the site-specific septation block mediated by the MinCDE system of *Escherichia coli. J. Bacteria* 174: 63-70 (1992).

de Haard, H. J. et al. A large non-immunized human Fab fragment phage library that permits rapid isolation and kinetic analysis of high affinity antibodies. *J. Biol. Chem.* 274: 18218-18230 (1999).

Devroe, E. and P. A. Silver Therapeutic potential of retroviral RNAi vectors. *Expert Opn. Biological Therapy* 4: 319 (2004).

Doige, C. A. and Ames, G. F. ATP-dependent transport systems in bacteria and humans: relevance to cystic fibrosis and multidrug resistance. *Annu. Rev. Microbiol.* 47: 291-319 (1993).

Dubel, S., Breitling, F., Kontermann, R., Schmidt, T., Skerra, A., Little, M. Bifunctional and multimeric complexes of streptavidin fused to single chain antibodies (scFv). *J. Immunol. Methods* 178: 201-209 (1995).

Dykxhoorn, D. M. and Lieberman, J. The silent revolution: RNA interference as basic biology, research tool, and therapeutic. *Annu. Rev. Med.* 56: 401-423 (2005).

Dykxhoorn, D. M., Palliser, D., Lieberman, J. The silent treatment: siRNAs as small molecule drugs. *Gene Ther.* 13: 541-552 (2006).

Elmén, J., Thonberg, H., Ljungberg, K., Frieden, M., Westergaard, M., Xu, Y., Wahren, B., Liang, Z., Ørum, H., Koch, T. and others. Locked nucleic acid (LNA) mediated improvements in siRNA stability and functionality. *Nucleic Acids Res.* 33: 439-447 (2005).

Enos, A. P., and Morris, N. R. Mutation of a gene that encodes a kinesin-like protein blocks nuclear division in *A. nidulans. Cell* 60: 1019-1027 (1990).

Glennie, M. J., McBride, H. M., Worth, A. T., Stevenson, G. T. Preparation and performance of bispecific Flab' gamma)2 antibody containing thioether-linked Fab' gamma fragments. *J. Immunol.* 39: 2367-2375 (1987).

Glover, D. M., Hagan, I. M., and Tavares, A. A. Polo-like kinases: a team that plays throughout mitosis. *Genes Dev.* 12: 3777-3787 (1998).

Gosselin, M. A. and Lee, R. J. Folate receptor-targeted liposomes as vectors for therapeutic agents. *Biotechnol. Annu. Rev.* 8: 103-131 (2002).

Gottesman, M., Fojo, T. and Bates, S. Multidrug resistance in cancer: role of ATP-dependent transporters. *Nature Rev. Cancer* 2: 48-58 (2002).

Griffiths, A. D. et al. Isolation of high affinity human antibodies directly from large synthetic repertoires. *EMBO J.* 13: 3245-3260 (1994).

Grishok, A., Tabara, H., Mello, C. C. Genetic requirements for inheritance of RNAi in *C. elegans*. *Science* 287: 2494-2497 (2000).

Guerrier-Takada, C., Gardiner, K., Marsh, T., Pace, N., Altman, S. The RNA moiety of ribonuclease P is the catalytic subunit of the enzyme. *Cell* 35: 849-857 (1983).

Hacein-Bey-Abina, S., Von Kalle, C., Schmidt, M., McCormack, M. P., Wulffraat, N., Leboulch, P., Lim, A., Osborne, C. S., Pawliuk, R., Morillon, E. et al. LMO2-associated clonal T cell proliferation in two patients after gene therapy for SCID-X1. *Science,* 302: 415-419 (2003).

Hampel, A. and Tritz, R. RNA catalytic properties of the minimum (-)sTRSV sequence. *Biochem.* 28: 4929-4933 (1989).

Hampel, A., Tritz, R., Hicks, M., Cruz, P. 'Hairpin' catalytic RNA model: evidence for helices and sequence requirement for substrate RNA. *Nucleic Acids Res.* 18: 299-304 (1990).

Hanada, M., Aime-Sempe, C., Sato, T., Reed, J. C. Structure function analysis of Bcl-2 protein. Identification of conserved domains important for homodimerization with Bcl-2 and heterodimerization with Bax. *J. Biol. Chem.* 270: 11962-11969 (1995).

Harry, E. J. Bacterial cell division: Regulating Z-ring formation. *Mol. Microbiol.* 40: 795-803 (2001).

Higgins, C. F. ABC transporters: physiology, structure and mechanism—an overview. *Res. Microbiol.* 152: 205-210 (2001).

Hiraga, S., Niki, H., Ogura, T., Ichinose, C., Mori, H., Ezaki, B., Jaffe, A. Chromosome partitioning in *Escherichia coli*: novel mutants producing anucleate cells. *J. Bacteriol.* 171: 1496-1505 (1989).

Hoshida, T., Sunamura, M., Duda, D. G., Egawa, S., Miyazaki, S., Shineha, R., Hamada, H., Ohtani, H., Satomi, S., Matsuno, S. Gene therapy for pancreatic cancer using an adenovirus vector encoding soluble flt-1 vascular endothelial growth factor receptor. *Pancreas* 25: 111-121 (2002).

Hu, Z. and Lutkenhaus, J. Topological regulation of cell division in *Escherichia coli* involves rapid pole to pole oscillation of the division inhibitor MinC under the control of MinD and MinE. *Mol. Microbiol.* 34: 82-90 (1999).

Hudson, P. J. and Souriau, C. Recombinant antibodies for cancer diagnosis and therapy. *Expert Opin. Biol. Ther.* 1: 845-855 (2001).

Hung, M. C., Hortobagyi, G. N., Ueno, N. T. Development of clinical trial of E1A gene therapy targeting HER-2/neu-overexpressing breast and ovarian cancer. *Adv. Exp. Med. Biol.* 465: 171-180 (2000).

Ireton, K., Gunther, N. W. $4^{th}$., Grossman, A. D. spo0J is required for normal chromosome segregation as well as the initiation of sporulation in *Bacillus subtilis*. *J. Bacteriol.* 176: 5320-5329 (1994).

Karpovsky, B., Titus, J. A., Stephany, D. A., Segal, D. M. Production of target-specific effector cells using hetero-cross-linked aggregates containing anti-target cell and anti-Fc gamma receptor antibodies. *J. Exp. Med.* 160: 1686-1701 (1984).

Knappik, A. et al. Fully synthetic human combinatorial antibody libraries (HuCAL) based on modular consensus frameworks and CDRs randomized with trinucleotides. *J. Mol. Biol.* 296: 57-86 (2000).

Jones, P. T., Dear, P. H., Foote, J., Neuberger, M. S., Winter, G. Replacing the complementarity-determining regions in a human antibody with those from a mouse. *Nature* 321: 522-525 (1986).

Kaetzel, C. S., Blanch, V. J., Hempen, P. M., Phillips, K. M., Piskurich, J. F., Youngman, K. R. The polymeric immunoglobulin receptor: structure and synthesis. *Biochem. Soc. Trans.* 25: 475-480 (1997).

Kapoor, T. M., Caner, T. U., Coughlin, M. L., Mitchison, T. J. 2000. Probing spindle assembly mechanisms with monastrol, a small molecule inhibitor of the mitotic kinesin, Eg5. *J. Cell Biol.* 150: 975-988 (2000).

Kleeff, J., Fukahi, K., Lopez, M. E., Friess, H., Buchler, M. W., Sosnowski, B. A., Korc, M. Targeting of suicide gene delivery in pancreatic cancer cells via FGF receptors. *Cancer Gene Ther.* 9: 522-532 (2002).

Kootstra, N. A. and Verma, I. M. (2003) Gene therapy with viral vectors. *Annu. Rev. Pharmacol. Toxicol.* 43: 413-439 (2003).

Kostelny, S. A., Cole, M. S., Tso, J. Y. Formation of a bispecific antibody by the use of leucine zippers. *J. Immunol.* 148: 1547-1553 (1992).

Kruh, G. D. and Belinsky, M. G. The MRP family of drug efflux pumps. *Oncogene* 22: 7537-7552 (2003).

Layzer, J. M., McCaffrey, A. P., Tanner, A. K., Huang, Z., Kay, M. A., Sullenger, B. A. In vivo activity of nuclease-resistant siRNAs. *RNA* 10: 766-771 (2004).

Lee, R. C., Feinbaum, R. L., Ambros, V. The *C. elegans* heterochronic gene lin-4 encodes small RNAs with antisense complementarity to lin-14. *Cell* 75: 843-854 (1993).

Marshall, J. Carcinoembryonic antigen-based vaccines. *Semin. Oncol.* 30: 30-36 (2003).

Caner, T. U., Kapoor, T. M., Haggarty, S. J., King, R. W., Schreiber, S. L., Mitchison, T. J. Small molecule inhibitor of mitotic spindle bipolarity identified in a phenotype-based screen. *Science* 286: 971-974 (1999).

McManus, M. T. and Sharp, P. A. Gene silencing in mammals by small interfering RNAs. *Nat. Rev. Genet.* 3: 737-747 (2002).

Miller, J. F. Bacterial transformation by electroporation. *Methods Enzymol.* 235: 375-385 (1994).

Modok, S., Mellor, H. R., Callaghan, R. Modulation of multidrug resistance efflux pump activity to overcome chemoresistance in cancer. *Curr. Opin. Pharmacol.* 6: 350-354 (2006).

Monia, B. P., Johnston, J. F., Sasmor, H., Cummins, L. L. Nuclease resistance and antisense activity of modified oligonucleotides targeted to Ha-ras. *J. Biol. Chem.* 271: 14533-14540 (1996).

Morrissey, D. V., Blanchard, K., Shaw, L., Jensen, K., Lockridge, J. A., Dickinson, B., McSwiggen, J. A., Vargeese, C., Bowman, K., Shaffer, C. S. and others. Activity of stabilized short interfering RNA in a mouse model of hepatitis B virus replication. *Hepatology* 41: 1349-1356 (2005).

Nicholson, R. I., Gee, J. M., Harper, M. E. EGFR and cancer prognosis. *Eur. J. Cancer* 37: S9-S15 (2001).

Nikaido, H. Prevention of drug access to bacterial targets: permeability barriers and active efflux. *Science* 264: 382-388. (1994).

Okada, Y., Wachi, M., Hirata, A., Suzuki, K., Nagai, K., Matsuhashi, M. Cytoplasmic axial filaments in *Escheri-* chia coli cells: possible function in the mechanism of chromosome segregation and cell division. *J. Bacteriol.* 176: 917-922 (1994).

Opalinska, J. B. and Gewirtz, A. M. Nucleic-acid therapeutics: basic principles and recent applications. *Nat. Rev. Drug Discov.* 1: 503-514 (2002).

Osbourn, J., Jermutus, L., Duncan, A. Current methods for the generation of human antibodies for the treatment of autoimmune diseases. *Drug Del. Tech.* 8: 845-851 (2003).

Pack, P. and Pluckthun, A. Miniantibodies: use of amphipathic helices to produce functional, flexibly linked dimeric Fv fragments with high avidity in *Escherichia coli. Biochemistry* 31: 1579-1584 (1992).

Paddison, P. J., A. Caudy, E. Bernstein, G. J. Hannon, D. C. Conklin Short hairpin RNAs (shRNAs) induce sequence-specific silencing in mammalian cells. *Genes & Development* 16: 948-958 (2002).

Perrotta, A. T. and Been, M. D. Cleavage of oligoribonucleotides by a ribozyme derived from the hepatitis delta virus RNA sequence. *Biochem.* 31: 16-21 (1992).

Pikaar, J. C., Voorhout, W. F., van Golde, L. M., Verhoef, J., Van Strijp, J. A., van Iwaarden, J. F. Opsonic activities of surfactant proteins A and D in phagocytosis of gram-negative bacteria by alveolar macrophages. *J. Infect. Dis.* 172: 481-489 (1995).

Raper, S. E., Chirmule, N., Lee, F. S., Wivel, N. A., Bagg, A., Gao, G. P., Wilson, J. M. and Batshaw, M. L. Fatal systemic inflammatory response syndrome in a ornithine transcarbamylase deficient patient following adenoviral gene transfer. *Mol. Genet. Metab.* 80: 148-158 (2003).

Raskin, D. M. and de Boer, P. A. MinDE-dependent pole-to-pole oscillation of division inhibitor MinC in *Escherichia coli. J. Bacteriol.* 181: 6419-6424 (1999).

Reeve, J. N. and Cornett, J. B. Bacteriophage SPO1-induced macromolecular synthesis in minicells of *Bacillus subtilis. J. Virol.* 15: 1308-1316 (1975).

Ridgway, J. B., Presta, L. G., Carter, P. 'Knobs-into-holes' engineering of antibody CH3 domains for heavy chain heterodimerization. *Protein Eng.* 9: 617-621 (1996).

Riechmann, L., Clark, M., Waldmann, H., Winter, G. Reshaping human antibodies for therapy. *Nature* 332: 323-327 (1988).

Riezman, H. Three clathrin-dependent budding steps and cell polarity. *Trends in Cell Biol.* 3: 330-332 (1993).

Rossi, J. J., Elkins, D., Zaia, J. A. Sullivan, S. Ribozymes as anti-HIV-1 therapeutic agents: principles, applications, and problems. *Aids Res. Human Retroviruses* 8: 183-189 (1992).

Salomon, D. S., Brandt, R., Ciardiello, F., Normanno, N. Epidermal growth factor-related peptides and their receptors in human malignancies. *Crit. Rev. Oncol. Hematol.* 19: 183-232 (1995).

Sandvig, K. and Deurs, B. Endocytosis without clathrin. *Trends in Cell Biol.* 4: 275-277 (1994).

Sawin, K. E. and Mitchison, T. J. Mutations in the kinesin-like protein Eg5 disrupting localization to the mitotic spindle. *Proc. Natl. Acad. Sci. USA* 92: 4289-4293 (1995).

Saville, B. J. and Collins, R. A. A site-specific self-cleavage reaction performed by a novel RNA in *Neurospora* mitochondria. *Cell* 61: 685-696 (1990).

Saville, B. J. and Collins, R. A. RNA-mediated ligation of self-cleavage products of a *Neurospora* mitochondrial plasmid transcript. *PNAS (USA)* 88: 8826-8830 (1991).

Sellers, W. R. and Fisher, D. E. Apoptosis in cancer drug targeting. *J. Clin. Invest.* 104: 1655-1661 (1999).

Sheets, M. D. et al. Efficient construction of a large nonimmune phage antibody library: the production of high-affinity human single-chain antibodies to protein antigens. *Proc. Natl Acad. Sci. USA* 95: 6157-6162 (1998).

Singh, M. Transferrin As A targeting ligand for liposomes and anticancer drugs. *Curr. Pharm. Des.* 5: 443-451 (1999).

Sioud, M. Therapeutic siRNAs. *Trends Pharmacol. Sci.* 25: 22-28 (2004).

Speert, D. P., Wright, S. D., Silverstein, S. C., Mah, B. Functional characterization of macrophage receptors for In-vitro phagocytosis of unopsonized *pseudomonas-aeruginosa. J. Clin. Invest.* 82: 872-879 (1988).

Stewart, P. S. and D'Ari, R. Genetic and morphological characterization of an *Escherichia coli* chromosome segregation mutant. *J. Bacteriol.* 174: 4513-4516 (1992).

Stockert, R. J. The asialoglycoprotein receptor: relationships between structure, function, and expression. Physiol. Rev. 75: 591-609 (1995).

Strebhardt, K., and Ullrich, A. Targeting Pololike kinase 1 for cancer therapy. *Nat. Rev. Cancer* 6: 321-330 (2006).

Sun et al. Overexpression of Bcl-2 blocks TNF-related apoptosis-inducing ligand (TRAIL)-induced apoptosis in human lung cancer cells. *Biochem. Biophys. Res. Commun.*, 280: 788 (2001).

Tao, W., South, V. J., Zhang, Y., Davide, J. P., Farrell, L., Kohl, N. E., Sepp-Lorenzino, L., Lobell, R. B. Induction of apoptosis by an inhibitor of the mitotic kinesin KSP requires both activation of the spindle assembly checkpoint and mitotic slippage. *Cancer Cell* 8: 49-59 (2005).

Thurnher, M., Wagner, E., Clausen, H., Mechtler, K., Rusconi, S., Dinter, A., Birnstiel, M. L., Berger, E. G., Cotton, M. Carbohydrate receptor-mediated gene transfer to human T leukaemic cells. *Glycobiology* 4: 429-435 (1994).

Todorovska, A. et al. *Design and application of diabodies*, triabodies and tetrabodies for cancer targeting. *J. Immunol. Methods* 248: 47-66 (2001).

Tomlinson, I. and Holliger, P. Methods for generating multivalent and bispecific antibody fragments. *Methods Enzymol.* 326: 461-479 (2000).

van de Weerdt, B. C., and Medema, R. H. Polo-like kinases: a team in control of the division. *Cell Cycle* 5: 853-864 (2006).

Vaughan, T. J., Osbourn, J. K., Tempest, P. R. Human antibodies by design. *Nature Biotechnol.* 16: 535-539 (1998).

Verhoeyen, M., Milstein, C., Winter, G. Reshaping human antibodies: grafting an antilysozyme activity. *Science* 239: 1534-1536 (1988).

Verma, I. M. and Weitzman, M. D. Gene therapy: twenty-first century medicine. *Annu. Rev. Biochem.* 74: 711-738 (2005).

Vickers, T. A., Koo, S., Bennett, C. F., Crooke, S. T., Dean, N. M., Baker, B. F. Efficient Reduction of Target RNAs by Small Interfering RNA and RNase H-dependent Antisense Agents. A COMPARATIVE ANALYSIS *J. Biol. Chem.* 278: 7108-7118 (2003).

Wachi, M., Doi, M., Okada, Y., Matsuhashi, M. New mre genes mreC and mreD, responsible for formation of the rod shape of *Escherichia coli* cells. *J. Bacteriol.* 171: 6511-6516 (1989).

Wang, C. Y., Cusack, J. C. Jr., Liu, R., Baldwin, A. S. Jr. Control of inducible chemoresistance: Enhanced anti-tumor therapy through increased apoptosis by inhibition of NF-κB. *Nat. Med.* 5: 412-417 (1999).

White, M. K., and McCubrey, J. A. Suppression of apoptosis: role in cell growth and neoplasia. *Leukemia* 15: 1011-1021 (2001).

Wright, S. D., Detmers, P. A., Jong, M. T., Meyer, B. C. Interferon-gama depresses binding of ligand by c3b and c3bi receptors on cultured human monocytes, an effect reversed by fibronectin. *J. Exp. Med.* 163: 1245-1259 (1986).

Wu, H., Hait, W. N., Yang, J. M. Small interfering RNA-induced suppression of MDR1 (P-glycoprotein) restores sensitivity to multidrug-resistant cancer cells. *Cancer Res.* 63: 1515-1519 (2003).

Yague, E., Higgins, C. F., Raguz, S. Complete reversal of multidrug resistance by stable expression of small interfering RNAs targeting MDR1. *Gene Ther.* 11: 1170-1174 (2004).

Zamore, P. D., Tuschl, T., Sharp, P. A., Bartel, D. P. RNAi: double-stranded RNA directs the ATP-dependent cleavage of mRNA at 21 to 23 nucleotide intervals. *Cell* 101: 25-33 (2000).

Zamore, P. D. Ancient pathways programmed by small RNAs. *Science* 296: 1265-1269 (2002).

Ziady, A. G., Perales, J. C., Ferkol, T., Gerken, T., Beegen, H., Perlmutter, D. H., Davis, P. B. Gene transfer into hepatoma cell lines via the serpin enzyme complex receptor. *Am. J. Physiol.* 273: G545-G552 (1997).

wherein the plurality comprises a therapeutically effective amount of the functional nucleic acid.

2. The composition of claim 1, wherein the functional nucleic acid is a regulatory RNA.

3. The composition of claim 2, wherein the regulatory RNA is selected from the group consisting of siRNA, miRNA, shRNA, antisense ssRNA, ribozyme, and decoy RNA.

4. The composition of claim 1, wherein the functional nucleic acid targets:
   (a) an RNA transcript encoding a protein that contributes to apoptosis resistance; or
   (b) an RNA transcript encoding a protein that contributes to neoplasticity.

5. The composition of claim 4 wherein:
   (a) the functional nucleic acid targets an RNA transcript encoding a protein that contributes to apoptosis resistance, wherein the transcript is of Bcl-2, Bcl-$X_L$, A1/Bfl 1, focal adhesion kinase or p53 protein; or
   (b) the functional nucleic acid targets an RNA transcript encoding a protein that contributes to neoplasticity, wherein the transcript is of β-Catenin, PKC-α, C-RAF,

We claim:

1. A composition comprising:
   (a) a plurality of intact minicells, each minicell of the plurality comprising plasmid-free functional nucleic acid, and
   (b) at least one pharmaceutically acceptable carrier, K-Ras, DP97 Dead box RNA helicase, cdk1, DNMT1, FLIP, C-Sfc, 53BPI, Polycomb group protein EZH2, ErbB1, HPV-16 E5, HPV-16 E7, Fortilin & MCl1P, KSP, DIP13α, MBD2, p21, KLF4, tpt/TCTP, SPK1 & SPK2, P300, PLK1, Trp53, Ras, ErbB1, VEGF, or BAG-1.

6. The composition of claim 1, further comprising a drug.

7. The composition of claim 6, wherein the functional nucleic acid targets a transcript encoding a protein that contributes to resistance to the drug.

8. The composition of claim 6, wherein the drug is packaged in an intact minicell.

9. The composition of claim 8, wherein the functional nucleic acid and the drug are packaged within the same minicell.

10. The composition of claim 1, further comprising a bispecific ligand, wherein the bispecific ligand comprises:
    (a) a first arm that carries specificity for a minicell surface structure, wherein the minicell surface structure is an O-polysaccharide component of a lipopolysaccharide on the minicell surface; and
    (b) a second arm that carries specificity for a non-phagocytic mammalian cell surface receptor.

11. The composition of claim 10, wherein the bispecific ligand comprises an antibody or an antibody fragment.

12. The composition of claim 1, wherein the composition comprises:
    (a) fewer than about 1 contaminating parent bacterial cell per $10^7$ minicells;
    (b) fewer than about 1 contaminating parent bacterial cell per $10^8$ minicells; or
    (c) fewer than about 1 contaminating parent bacterial cell per $10^9$ minicells.

13. A method of delivering functional nucleic acid to a target mammalian cell, comprising:
    (a) providing a plurality of intact minicells in a pharmaceutically acceptable carrier, each minicell of the plurality comprising plasmid-free functional nucleic acid, and
    (b) contacting minicells of the plurality with the target mammalian cells such that the mammalian cells engulf minicells of the plurality, whereby the functional nucleic acid is released into the cytoplasm of the mammalian cells.

14. The method of claim 13, wherein the functional nucleic acid is a regulatory RNA.

15. The method of claim 14, wherein the regulatory RNA is selected from the group consisting of siRNA, miRNA, shRNA, antisense ssRNA, ribozyme, and decoy RNA.

16. The method of claim 13, wherein at least a portion of the plurality comprises a therapeutically effective amount of the functional nucleic acid.

17. The method of claim 13, wherein the functional nucleic acid targets a transcript selected from the group consisting of:
    (a) encoding a protein that contributes to drug-resistance;
    (b) of P-glycoprotein, MDR-2 or MDR-3;
    (c) of MRP2, BCR-ABL, STI-571 resistance-associated protein, lung resistance-related protein, cyclooxygenase-2, nuclear factor kappa, XRCC1, ERCC1, GSTP1, mutant β-tubulin, or a growth factor;
    (d) of a protein that contributes to apoptosis resistance;
    (e) of Bcl-2, Bcl-$X_L$, A1/Bfl 1, focal adhesion kinase or p53 protein;
    (f) of a protein that contributes to neoplasticity; and
    (g) of β-Catenin, PKC-α, C-RAF, K-Ras, DP97 Dead box RNA helicase, cdk1, DNMT1, FLIP, C-Sfc, 53BPI, Polycomb group protein EZH2, ErbB1, HPV-16 E5 and E7, Fortilin & MCl1P, DIP13α, KSP, MBD2, p21, KLF4, tpt/TCTP, SPK1 & SPK2, P300, PLK1, Trp53, Ras, ErbB1, VEGF, or BAG-1.

18. The method of claim 13, further comprising step (c) delivering a drug to the target mammalian cell.

19. The method of claim 18, wherein the functional nucleic acid targets the transcript of a protein that contributes to resistance to the drug.

20. The method of claim 19, wherein the drug is packaged in an intact minicell.

21. The method of claim 20, wherein the functional nucleic acid and the drug are packaged within the same minicell.

22. The method of claim 18, wherein step (c) occurs subsequent to steps (a) and (b).

23. The method of claim 18, wherein the drug is delivered concurrently with step (b).

24. The method of claim 13, wherein step (b) comprises contacting a bispecific ligand with at least some of the intact minicells and the target mammalian cell, such that the bispecific ligand causes minicells to bind to the mammalian cell.

25. The method of claim 24, wherein the target mammalian cell is a non-phagocytic cell.

26. The method of claim 24, wherein the bispecific ligand comprises:
    (a) a first arm that carries specificity for a minicell surface structure, wherein the minicell surface structure is an O-polysaccharide component of a lipopolysaccharide on the minicell surface; and
    (b) a second arm that carries specificity for a non-phagocytic mammalian cell surface receptor.

27. The method of claim 26, wherein the mammalian cell surface receptor is capable of activating receptor-mediated endocytosis of the minicell.

28. The method of claim 24, wherein the bispecific ligand comprises an antibody or antibody fragment.

29. The method of claim 13, wherein the mammalian cell is phagocytosis- or endocytosis-competent.

30. A method for formulating a minicell of the composition of claim 1, comprising co-incubating a plurality of intact minicells with functional nucleic acid in a buffer.

31. The method of claim 30, wherein the functional nucleic acid is a regulatory RNA.

32. The method of claim 31, wherein the regulatory RNA is selected from the group consisting of siRNA, miRNA, shRNA, antisense ssRNA, ribozyme, and decoy RNA.

33. The method of claim 30, wherein the co-incubation comprises gentle shaking.

34. The method of claim 30, wherein the co-incubation lasts about 0.5 hour or about 1 hour.

35. The method of claim 30, wherein the buffer comprises:
    (a) buffered saline;
    (b) buffered saline in gelatin form; or
    (c) a 1× phosphate buffer solution.

36. The method of claim 30, wherein the co-incubation is conducted at a temperature selected from the group consisting of:
    (a) about 4° C. to about 37° C.;
    (b) about 20° C. to about 30° C.;
    (c) about 25° C.; or
    (d) about 37° C.

37. The method of claim 30, wherein the co-incubation comprises about $10^7$, about $10^8$, about $10^9$, about $10^{10}$, about $10^{11}$, about $10^{12}$ or about $10^{13}$ minicells.

38. The composition of claim 1, wherein there is an absence from the minicells of a construct for in situ expression of the functional nucleic acid.

39. A composition comprising:
    (a) a plurality of intact minicells, each minicell of the plurality comprising functional nucleic acid, wherein there is an absence from the minicells of a construct for in situ expression of the functional nucleic acid, and
(b) at least one pharmaceutically acceptable carrier.

\* \* \* \* \*